US007918229B2

(12) United States Patent
Cumbie et al.

(10) Patent No.: US 7,918,229 B2
(45) Date of Patent: *Apr. 5, 2011

(54) METHOD AND DEVICE TO INACTIVATE AND KILL CELLS AND ORGANISMS THAT ARE UNDESIRABLE

(75) Inventors: William E. Cumbie, Yorktown, VA (US); Douglas B. Juanarena, Blacksburg, VA (US)

(73) Assignee: Keraderm Corp., Blacksburg, VA (US)

( * ) Notice: Subject to any disclaimer, the term of this patent is extended or adjusted under 35 U.S.C. 154(b) by 275 days.

This patent is subject to a terminal disclaimer.

(21) Appl. No.: 11/785,111

(22) Filed: Apr. 16, 2007

(65) Prior Publication Data

US 2007/0255266 A1 Nov. 1, 2007

Related U.S. Application Data

(63) Continuation-in-part of application No. 11/154,707, filed on Jun. 17, 2005, now Pat. No. 7,306,620, which is a continuation-in-part of application No. 10/215,834, filed on Aug. 9, 2002, now Pat. No. 6,960,201, application No. 11/785,111, which is a continuation-in-part of application No. 11/185,791, filed on Jul. 21, 2005, now Pat. No. 7,494,502.

(60) Provisional application No. 60/355,088, filed on Feb. 11, 2002, provisional application No. 60/792,331, filed on Apr. 17, 2006, provisional application No. 60/810,167, filed on Jun. 2, 2006, provisional application No. 60/844,642, filed on Sep. 15, 2006.

(51) Int. Cl.
*A61B 19/00* (2006.01)

(52) U.S. Cl. .............................. 128/898; 607/88; 606/9

(58) Field of Classification Search ................ 606/3–31, 606/130, 131; 607/88–95; 128/898
See application file for complete search history.

(56) References Cited

U.S. PATENT DOCUMENTS

| 6,050,990 | A | * | 4/2000 | Tankovich et al. | 606/9 |
| 6,090,788 | A | * | 7/2000 | Lurie | 514/23 |
| 6,129,893 | A | * | 10/2000 | Bolton et al. | 422/23 |
| 6,255,324 | B1 | * | 7/2001 | Heindel et al. | 514/314 |
| 6,283,986 | B1 | * | 9/2001 | Johnson | 607/94 |
| 6,379,376 | B1 | * | 4/2002 | Lubart | 607/88 |

(Continued)

OTHER PUBLICATIONS

International Search Report; PCT/US2008/082182, Mar. 20, 2009.

(Continued)

*Primary Examiner* — Ahmed M Farah
(74) *Attorney, Agent, or Firm* — Merek, Blackmon & Voorhees, LLC

(57) ABSTRACT

A method, means, and apparatus to prevent and treat infections and disorders using germicidal light to inactivate and/or kill the organisms or cells that cause infections and other disorders. The method of treatment comprises irradiating the area to be treated using electromagnetic radiation of a germicidal nature. The method utilizes a previously unrecognized ability of germicidal light to penetrate the skin, nails, and other membranes sufficiently to successfully treat and prevent disorders. The electromagnetic radiation damages the organisms and cells that cause disorders such as skin and nail infections and renders them substantially incapable of reproducing. Without the ability to replicate the organism cannot continue to infest the skin and nails. The damage inflicted can also be sufficient to kill the organism outright. An infection is thereby prevented (if organisms are present, but infection has not yet begun), and the infection is cured if the infection already exists.

5 Claims, 4 Drawing Sheets

U.S. PATENT DOCUMENTS

| | | | |
|---|---|---|---|
| 6,464,625 B2 * | 10/2002 | Ganz | 600/3 |
| 6,663,658 B1 * | 12/2003 | Kollias et al. | 607/88 |
| 6,663,659 B2 * | 12/2003 | McDaniel | 607/88 |
| 6,960,201 B2 * | 11/2005 | Cumbie | 606/9 |
| 7,033,381 B1 | 4/2006 | Larsen | |
| 7,177,695 B2 * | 2/2007 | Moran | 607/50 |
| 2003/0157073 A1 * | 8/2003 | Peritt et al. | 424/93.21 |
| 2006/0004425 A1 * | 1/2006 | Cumbie | 607/86 |
| 2006/0173515 A1 * | 8/2006 | Cumbie | 607/88 |
| 2006/0206173 A1 | 9/2006 | Gertner et al. | |
| 2007/0005047 A1 | 1/2007 | Ferren et al. | |
| 2007/0043406 A1 * | 2/2007 | Tolkoff et al. | 607/88 |
| 2007/0231255 A1 | 10/2007 | Barolet et al. | |
| 2007/0255266 A1 | 11/2007 | Cumbie et al. | |

OTHER PUBLICATIONS

International Preliminary Report on Patentability; PCT/US2008/082182, Sep. 1, 2009.

* cited by examiner

METHOD AND DEVICE TO INACTIVATE AND KILL CELLS AND ORGANISMS THAT ARE UNDESIRABLE

1 CROSS-REFERENCE TO RELATED APPLICATIONS

This application is a continuation in part of U.S. application Ser. No. 11/154,707, filed Jun. 17, 2005 now U.S. Pat. No. 7,306,620, which is a continuation in part of U.S. patent application Ser. No. 10/215,834, filed Aug. 9, 2002, now U.S. Pat. No. 6,960,201, which claims the benefit of U.S. Provisional Application 60/355,088, filed Feb. 11, 2002, all of which are incorporated herein by reference. The application is also a continuation in part of U.S. application Ser. No. 11/185,791, filed Jul. 21, 2005 now U.S. Pat. No. 7,494,502, which is incorporated herein by reference. This application also claims benefit of U.S. Provisional Applications Ser. No. 60/792,331, filed Apr. 17, 2006, Ser. No. 60/810,167, filed Jun. 2, 2006, and Ser. No. 60/844,642, filed Sep. 15, 2006, each of which are incorporated herein by reference.

BACKGROUND

Germicidal light has been used for many years to inactivate and kill organisms found in air and water and to sterilize surfaces. Ultraviolet light in the 'C' range of 240 nm to 280 nm (also called the "UVC range") is recognized as the most germicidal of all light. However, due to its short wavelength, UVC does not penetrate substances very deeply. For example, the sun emits a large amount of UVC, however, no UVC reaches the earth's surface because it is completely absorbed in the atmosphere. Literature on UVC notes that it cannot significantly penetrate any medium besides air and relatively clean water due to its short wavelength. This lack of penetration has prevented those skilled in the art from trying to use UVC to inactivate or kill organisms in tissue. It has also caused those skilled in the art to research forms of germicidal light other than UVC that may be more capable of penetrating tissue and other mediums.

2 SUMMARY AND OBJECTS AND ADVANTAGES OF THE INVENTION

The present invention, a method, means, and apparatus to prevent and treat infections and disorders, uses germicidal light to inactivate and/or kill the organisms or cells that cause infections and other disorders. The method of treatment comprises irradiating the area to be treated using electromagnetic radiation of a germicidal nature. The method utilizes a previously unrecognized ability of germicidal light to penetrate the skin, nails, and other membranes sufficiently to successfully treat and prevent disorders. Said electromagnetic radiation damages the organisms and cells that cause disorders such as skin and nail infections and renders them substantially incapable of reproducing. Without the ability to replicate the organism cannot continue to infest the skin and nails. The damage inflicted can also be sufficient to kill the organism outright. An infection is thereby prevented (if organisms are present, but infection has not yet begun), and the infection is cured if the infection already exists.

The method of the invention may thus include one or more of the following steps: diagnosing an infection or potential infection; determining the location of the infection, especially in skin or nail; testing transmissivity of the tissue surrounding the location to light; calculating an amount of light necessary to achieve the proper dosage at the infected area, especially a location beneath an amount of skin or nail; selecting a light source to be used; selecting a filter to filter a portion of the light; modifying the light to enhance its effectiveness; directing the light to the appropriate area, such as by using shields or light guides; supplementing the light treatment; applying treatment cycles; and repeating some or all of the steps as necessary.

In some embodiments, the light source may be a narrowband light source. In some embodiments, the light source may be a broadband light source. In some embodiments, light may be modified by at least one of pulsing, combing light sources, filtering the light, modulating the light, and evaluating the energy of the light. In certain embodiments, light may be directed to a particular area by a shield or light guide. In some embodiments, the method of the invention can be supplemented with additional treatments including, but not limited to, antiobiotics, antibodies, and chemotherapeutic agents. In certain embodiments, light may be provided in treatment cycles, which include, but are not limited to, applying multiple types of light sequentially, applying multiple types of light in parallel, and applying light in periodic does.

In some embodiments, germicidal light can be used to inactivate and kill undesirable cells in the treatment. The term "inactivate," as used throughout, refers to rendering an organism incapable of reproducing. A population of organisms is "substantially incapable of reproducing" when enough organisms have been inactivated that they are unable to maintain a viable population and thus dwindle until the remaining organisms cannot sustain an infection. The term "kill," as used throughout, refers to the cessation of metabolic processes in the organism. This targeted inactivation and killing of undesirable cells can be used to treat disorders such as cancer, tumors, and autoimmune disorders such as psoriasis. See for example U.S. Provisional Application 60/844,642 filed Sep. 15, 2006, which is incorporated herein by reference, to William Cumbie, which discusses treatment of cancer using UV light, including among other things, treatment of skin cancer. This type of treatment has not been used earlier by those skilled in the art because it was felt that germicidal light could not penetrate deeply enough to be effective and because the most potent germicidal light (UV) can be carcinogenic. However, advances in unrelated fields combined with new research resulting from the inventor has shown that the penetration of germicidal light can be enhanced and even without enhancement the small amount if light that penetrates is sufficient to be efficacious to a high degree. The potential carcinogenicity of UV light has deterred those skilled in the art from pursuing it as a treatment for cancer itself. Cancer, however, is more likely from repeated exposures than from a few targeted treatments using UV light. Thus, although there were several reasons why those skilled in the art did not pursue this type of treatment, this novel way of thinking about treatment permits the invention to be used efficaciously to treat these infections and disorders of the skin and nails. Additionally, this invention can be used to inactivate and kill organisms that cause infections, to disinfect wounds, or to cure warts, acne, etc.

Therefore it can be an object of the invention to treat an infection or prevent infection by treating a patient using germicidal light. This treatment can be used instead of surgery, radiation, or chemotherapy. By avoiding the use of these more invasive procedure, significant side effects can be avoided.

It can be another object of the invention to treat an infection or prevent infection by treating a patient, by applying germicidal light that can be applied more quickly and precisely as compared to surgery, radiation, or chemotherapy.

It can be a further object of the invention to treat an infection or prevent infection by treating a patient with germicidal light that can be used in conjunction with other therapies such as surgery, radiation, and chemotherapy to increase their efficacy.

It can be yet another object of the invention to treat an infection or prevent infection by treating a patient using germicidal light that can be conditioned to permit it to better penetrate solid media, improving the efficacy of treatment. In some embodiments, light can be conditioned by using multichromatic light. In some embodiments, light can be conditioned by using a strobe light.

It is also can be an object of the invention to treat an infection or prevent infection by treating a patient by applying germicidal light that can be conditioned to make it more lethal to organisms and cells which improves the efficacy of treatment, including using wide spectrum light.

Additionally, it is an object of the invention to apply germicidal light to inactivate and kill organisms that cause infections, wounds, warts, acne, etc.

These objects of the present invention are not exhaustive and are not to be construed as limiting the scope of the claimed invention. No one embodiment need encompass all of the objects or any of the objects.

3 DRAWINGS

Figure 1:
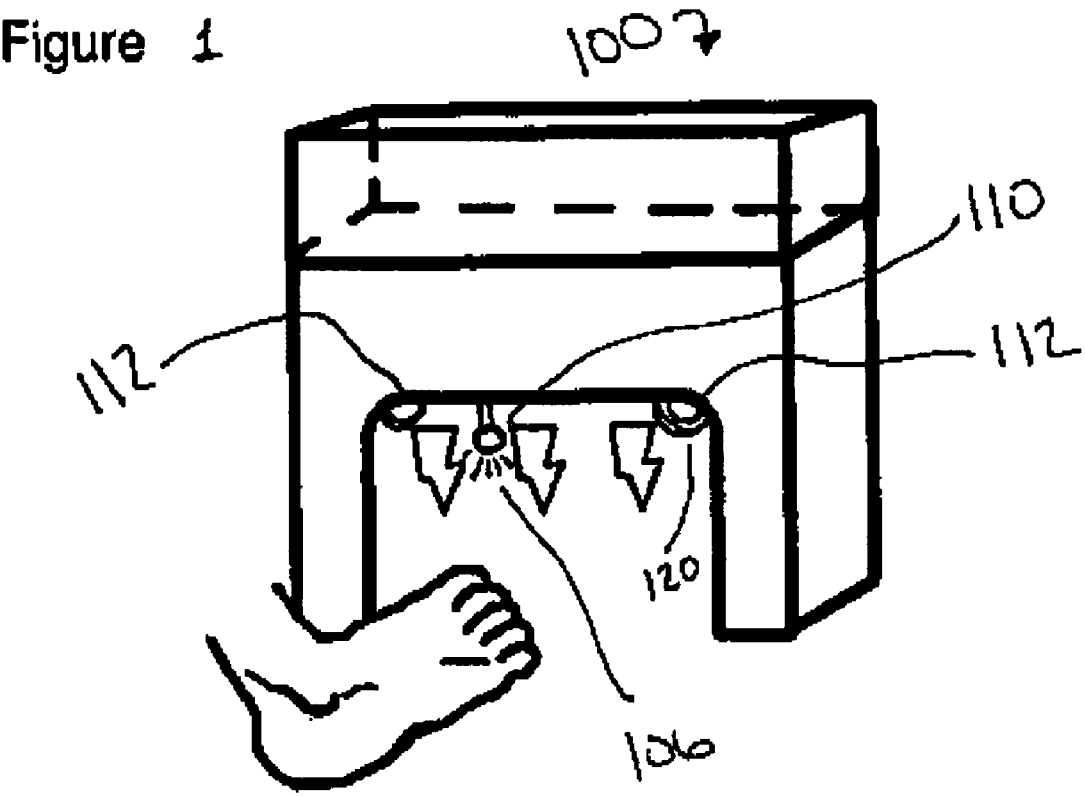
FIG. 1 is a diagrammatic view of a light according to an embodiment of the present invention for use in treating skin or nail.

These drawings are illustrative or representative treatments and are not intended to be exhaustive. Those skilled in the art will readily discern additional applications that are covered by this technology and are therefore included in this disclosure such as treatment of warts, superficial skin infections, etc.

4 DETAILED DESCRIPTION

To achieve the objects of the invention, the invention takes advantage of the previously unrecognized fact that although it is true that UVC does not penetrate tissue easily, a small amount can penetrate for a short distance into relatively solid material such as tissue and nails. The small amount of UVC light that does penetrate does so well enough to inactivate or kill cells that are undesirable. This is an unexpected result and forms one of the foundations for the novel use of germicidal light to treat skin and nail infections. See Cumbie, U.S. Pat. No. 6,960,201 which is incorporated herein by reference.

Ultraviolet (UV) light can also be carcinogenic. It is therefore unobvious and unexpected that UV light may be used successfully to treat cancerous cells. This has prevented UV light from being researched as a cure for cancer—particularly skin cancer, which appears to be caused by exposure to sunlight—particularly UV light. However, it is the chronic exposure to ultraviolet light that is the greatest cause of its carcinogenicity. Acute exposure is not as carcinogenic as chronic exposure because it does not expose cells to UV light repeatedly thereby causing mutations that eventually evolve into cancerous cells.

The invention disclosed in this application can also be used to inactivate or kill cells that have become detrimental to health, such as cancer cells and tumors. Furthermore, this invention can be used to inactivate organisms that can cause disease, infections, wounds, and other disorders.

4.1 UVC Light Dose Necessary to Inactivate Microbes

UVC light has the ability to inactivate organisms by damaging the organism's genetic material, which in turn prevents it from reproducing. Inactivation energies for organisms using UVC light alone vary from less than 1 mj/cm2 to greater than 100,000 mj/cm$^2$. This is a very wide range, however, most organisms tend to be inactivated in the lower 1% of this range, i.e., 1 mj/cm$^2$ to 1,000 mj/cm$^2$ (1 j/cm$^2$).

The EPA guidance manual on Alternate Disinfectants and Oxidants (April 1999) devotes Chapter 8 to a discussion of germicidal UV as a disinfectant for drinking water. The manual notes that a UV wavelength of 240 to 280 nm is highly absorbed by the RNA and DNA of a microorganism. The absorbance of UV by the organisms results in the damage to the organism's ability to reproduce. The damage is often caused by the dimerization of pyrimidine molecules. A dimer is a molecule consisting of two identical simpler molecules and dimerization is the process of linking the two molecules together. Dimerization of the pyrimidine molecules distorts the DNA helical structure. The EPA guidance manual also notes that the dose to inactivate 90% of most types of organisms is very low with a typical range of 2 to 6 mJ/cm$^2$. The manual notes that the germicidal radiation can be generated by a number of sources including a low pressure mercury lamp emitting at 254 nm, a medium pressure lamp emitting at 180 to 1370 nm, or lamps that emit at other wavelengths in a high intensity pulsed manner.

4.2 Wide Spectrum Germicidal Light

Wide spectrum light has germicidal properties and can offer some advantages over the use of narrowband UV light. These advantages can include the following:

a. Although the UV component of polychromatic light still does not penetrate easily, other wavelengths can penetrate better and thus contribute relatively more than usual to inactivating organisms. Thus, polychromatic radiation has the potential to inactivate organisms using less energy in the UVC range than would be required using UVC light alone.

b. Polychromatic light or light containing multiple wavelengths can act on various processes of the cells and cause inactivation of organisms at lower energies than ultraviolet light alone. In addition to greater inactivation of organisms using polychromatic light, the inactivation of a wider variety of organisms is possible since the multiple bands of light affect each type of organism differently and will thus affect a wider variety of organisms.

c. Because different wavelengths are absorbed by different part of each organism, the use of multiple wavelengths increases the chance that structures that are essential to the organism will be inactivated thus rendering the organism harmless.

Wideband UVC light, defined as light that covers the entire UVC spectrum of 240 nm to 280 nm (as opposed to monochromatic UVC light that emits primarily at one wavelength, such as 254 nm for a low pressure mercury lamp) has germicidal properties and offers advantages to the use of narrowband UV light. These advantages include the following:

a. Since all of the UVC range exhibits strong germicidal properties, it is possible to spread the dosage over the entire band, limiting the amount of light that is delivered at any one wavelength. This can help alleviate any negative responses to the UV (such as erythema).

b. While the optimal range of UVC for inactivation of organisms due to the formation of pyrimidine dimers is at centered about 258 nm, research indicates that various organisms are more affected at other ranges of the UVC spectrum. Use of broad band UVC across the range of 240 nm and 280 nm ensures that energy is delivered at wavelengths to which all organisms are susceptible.

Pulsed light variants of polychromatic and UVC light also have germicidal properties and can offer advantages over the use of narrowband UV light. These advantages can include the following:

a. Applicant's laboratory data shows that high intensity pulses are significantly more effective at penetrating tissue than when the same amount of continuous monochromatic light is applied over a longer period of time. Other research that Applicant has performed indicates that pulsing of high-energy, wide spectrum light can increase the depth of penetration through tissue by several orders of magnitude compared to continuous monochromatic light. This finding, which is not common knowledge to those skilled in the art of treating skin and other body disorders, permits the novel use of pulsed light to inactivate organisms at a much lower dose of UVC than continuously emitting light.

b. Since pulsed light can be more effectively used to penetrate tissue and inactivate organisms, it can substantially reduce the time necessary for treatment.

c. Additionally, since the pulsed light can be used to more effectively to penetrate tissue, it can be used to treat infections that are substantially deeper than surface infections.

d. Pulsed light emits significantly higher energy in a very short time period compared with continuous light. These short, high intensity pulses appear to overwhelm cells and damage vital components that are unable to dissipate the excess instantaneous energy being applied. Additionally, short pulses of light with comparatively longer periods of low light or no light permit time for energy to dissipate and thus limits the amount of heat experienced by surrounding tissues, thereby limiting collateral damage e. The very high peak of the energy pulse is often several orders of magnitude greater than the average energy applied. This high peak dose is more likely to exceed the threshold energy (also called the energy of activation), thereby driving reactions that would not begin until this threshold is reached. Thus, these peak doses can trigger reactions that will contribute to the inactivation of organisms by damaging vital components or forming compounds that are antibiotic in nature such as singlet oxygen or ozone.

f. Pulsed light can damage undesirable cells with a lower overall doses since the pulsed light can deliver extremely high doses that overwhelm the cell in short pulses, yet with substantial time periods ("down time") between pulses. Thus an organism may be exposed to a peak of several orders of magnitude greater than if the light were uniformly spread over time.

Coherent light variants of polychromatic and UVC light such as lasers also have germicidal properties and can offer advantages to the use of narrowband UV light. These advantages can include the following:

a. Lasers can be pulsed to offer the same advantages that other pulsed light sources possess, namely they can penetrate better than continuous light.

b. All lasers make use of coherent light of a very narrow band. The lasers can thus be tuned to do the most damage to infectious organisms while not affecting other organisms as greatly. For example, if a particular organism is best deactivated at a wavelength of 245 nm, a tunable laser could be used to deliver light precisely at the 245 nm wavelength. Surrounding tissue and organisms would not be as greatly affected since most typical organisms are affected most strongly between 258 nm and 262 nm.

4.3 Pulsed Polychromatic Light Dose Necessary to Inactivate Microbes

While most wavelengths are not germicidal by themselves, they can have synergistic effects that aid in inactivating organisms. When combined with the germicidal effects of UVC light, multichromatic sources can often lower by up to an order of magnitude or more the required dose of the potentially harmful UVC. Xenon flash lamps can be a particularly attractive source of multichromatic light because in addition to providing multiple wavelengths of light, the xenon flash lamps can be pulsed to provide extremely high momentary doses of light allowing the light to be safely delivered repeatedly via a strobe mode. Multichromatic light can have the following advantages, especially when a characteristic of the emitted light has been altered to enhance the properties of the light. A "light characteristic" is a property of light. Light characteristics include but are not limited to, wavelength, energy, penetration, frequency of exposure (pulsing), length of exposure, etc.

a. High peak doses—very high peak doses can be delivered using high energy pulses that have short durations. The overall energy applied can still be lower on average than applied by a continuous lamp, however, the peak doses could be 10 to 1,000,000 times or more the average dose. The high peak doses can act as a 'punch' to cause damage that might not be accomplished at lower energies. An analogy would be applying pressure to drive a nail through a piece of wood. If a person pushed on a nail with his hand for days he may not be able to drive a nail through wood. However, a strong momentary blow to the nail delivered via a hammer can drive the nail quickly. The total amount of energy applied by hand to the nail could actually be greater but the momentary energy application via a hammer is more likely to successfully drive the nail. In the same way high peak doses have the ability to damage the genetic material quickly and effectively without the use of high average doses. Recent laboratory data indicate that a dosage applied as a high-energy, pulsed strobing of light can increase its ability to penetrate tissue by several orders of magnitude.

b. Repetitive pulsating doses—a lamp that is pulsed, or strobed, can deliver over one hundred intense pulses per second or more. These pulses have the effect of rapidly changing the environment of the organism and also affecting its biological processes. The repetitive fluctuations can do damage that continuous light might not accomplish, while at the same time protecting the surrounding skin from deleterious effects that other forms of light at the same dosage might cause. An analogy would be the flexing of a piece of metal. While it might flex once or for a dozen times without breaking, continuous flexing of a piece of metal will cause it to fatigue and eventually break. With pulsed light, the strobing of light at multiple pulses per second can affect this type of fatigue and failure in an organism in a short period of time. The strobing may also create harmonic waves, which can do additional damage to the cellular processes of the organism.

c. High Voltage Pulsing—Pulsing with very high voltage can shift the spectra of the light to shorter wavelengths and dramatically increase the amount of light emitted in the UV range, which is also the wavelength that has been found to be the most germicidal. High voltage pulsing can deliver an extremely high peak dose (generally peaks measured in megawatts) in a very small time period (generally time periods of microseconds). For example, the RC-700 that was used in pilot clinical trials discussed in this application delivered a 0.2 megawatt (200,000 watts) peak power dose when the average power was only 600 watts which makes the peak dose approximately 333 times the average dose (note this data is input power, not light energy output). Additionally, this pulse was delivered via pulses that had a width of 25 microseconds with 120 pulses delivered per second. Thus, the total 'on' time of the lamp was 3 milliseconds per second, or to put it another way the lamp was 'on' only 0.3% of the time. This equates to a peak instantaneous dose of more than one hundred thousand times the average dose if the same light had been applied at a constant rate with no pulsing.

4.4 Preferred Methods and Apparatus of the Invention

Referring to the drawings, a method and means for the prevention and treatment of undesirable cells and organisms is shown. The method, as seen in FIG. 1, includes irradiating a target tissue 104, such as a skin or nail, with light 106. The procedure uses specific types and levels of light having a germicidal electromagnetic radiation component to take advantage of the previously unrecognized ability of radiation to penetrate tissues and other matter sufficiently to inactivate organisms and undesirable cells without unduly harming the host (e.g., human or animal patient). It should be noted that in addition to killing a cell or organism, said method and means can also keep activation dose at a safe ("lower") level by inactivating an organism.

This method and means also combines the previously unrecognized ability of pulsing of light to significantly enhance the light's ability to penetrate tissue and to increase the efficacy of said germicidal light. The method also makes use of the enhanced efficacy of pulsed light to inactivate cells by disruption of essential cellular processes due to the light's 'strobing' effect and its high energy peak pulses. The method and means to inactivate cells and organisms also includes the novel combination of using polychromatic light combined with filters that prevent undesirable bandwidths from reaching the area to be treated.

The following descriptions of the invention are not intended to limit the scope of the invention but are made merely for the purpose of describing general principles of the invention. Further, it must be understood that no one embodiment of the present invention need include all of the aforementioned objects of the present invention or the features of the preferred embodiment of the invention. Rather, a given embodiment may include one or none of the objects or features. Accordingly, the preferred embodiments and objects of the invention are not to be used to limit the scope of the claims of the present invention.

4.5 Description of Device to Prevent and Treat Infections

As shown in FIG. 1, a device 100 to prevent and treat infections can incorporate a number of special features to enhance treatment and promote safety. For example the treatment device may contain a light source 110 that can be tuned to a specific spectral output or has a fixed spectral output 106.

Figure 2:
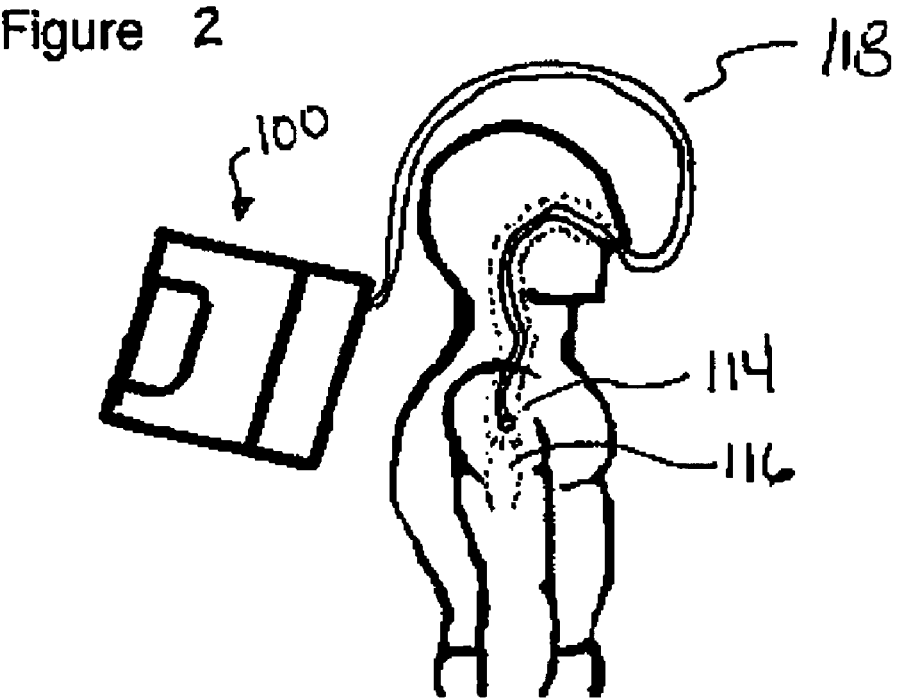
FIG. 2 is a diagrammatic view of a light according to an embodiment of the present invention for use in treating an internal orifice.

This can be accomplished by the use of a tunable laser, multiple lamps, or by the use of one or more filters to screen out wavelengths that are not desirable. A combination of lamps and sources 110,112 may also be used. The treatment device may also contain very small lamps 114 (FIG. 2) capable of being inserted in small spaces 116 or directly on the surface to be treated. This will permit its use to treat orifices or internal passageways 116 that may be affected such as the pulmonary tract or the digestive tract. Light can also be concentrated and transmitted via a light guide 118 thus permitting high doses to be precisely applied to the area to be treated. Several attachments may be added to the device to permit light to be directed to the area to be treated including attachments 120 that evenly diffuse light to a larger area being treated or to direct and concentrate light to a smaller area being treated. Attachments 118 can also be used that are flexible and conform to the area being treated and are capable of transmitting light to the area being treated.

The treatment device can use polychromatic light to prevent and treat infections. This light may be conditioned in a number of ways to make it more efficacious and safer. For example, the light can be pulsed to achieve an improvement in efficacy of three orders of magnitude or more. Also, the unwanted bandwidths of the light can be filtered out to improve the safety of the device.

The treatment device can also use monochromatic light or narrowband light to treat cells or organisms. This light can be provided by a polychromatic light source that is filtered to provide only a limited bandwidth, a tunable laser, or a monochromatic light source such as some excimer lamps emit or that a low pressure mercury lamp would emit.

It should be noted that the device can be used to treat animals as well as humans. In fact, the ability of pulsed light to enhance penetration greatly increases the devices efficacy for animals that have thicker hides or nails (e.g., hoofs or claws).

4.6 Mechanisms of Inactivation

It has been noted in co-pending U.S. application Ser. No. 11/185,791, filed Jul. 21, 2005, that there is a distinct difference in destroying an organism or cell by heating the entire organism and by destroying it by damaging its genetic material. "Thermocide," as used in this application, is defined as a method of inactivating or killing an organism, where the main cause of destruction is by heating the entire organism. "Geneticide," as used in this application, is defined as destroying an organism by damaging its genetic material, which kills or inactivates the organism. Geneticide may require a much lower level of electromagnetic radiation to achieve. Thus, the treatment and device described in this application does not rely on thermocide to inactivate an organism or cell. Instead the primary mode of inactivation of a cell or organism is by geneticide.

It should be noted that although damage to the genetic material of a cell is the major cause of geneticide, other processes can contribute to this process, which are not directly genetic such as destruction of MRNA and the rupture of cell membranes. Thus, DNA or RNA is "directly altered" when the treatment damages the genetic material containing all the genes of the organism.

In addition to geneticide as defined herein, and explained in the Ser. No. 11/185,791 application, it is possible to also kills cells or organisms solely by destroying structures vital to the existence of a cell or organism. Examples include destruction of membranes, ribosomes, mitochondria, and other structures that the cell or organism require. Additionally, it is possible to damage but not destroy a number of said structures where the damage to any one structure would not normally result in the inactivation of the cell or organism but the combination of damage is sufficient to inactivate the organism. In all of these cases, heating the entire organism does not facilitate inactivation. Rather, cumulative damage or destruction of specific components of the cell or organism leads to death or inactivation. While this may be accompanied by instantaneous heating of these components the entire organism is not uniformly heated to destroy it outright by excessive heat. It should be noted that while the temperature of the tissue surrounding the treated area may rise, this temperature rise is less than what is sufficient to destroy the cells or organisms by excessive heat alone. This damage or destruction of vital components of the cell or organism is included in the definition of the term "cell death."

4.7 Enhanced Penetration of Germicidal Radiation through Tissues by Use of Pulsed Polychromatic Light As noted above there has been virtually no published research on optimizing the transmission of UVC through tissues. Optimizing the penetrating power of UVC opens up a much wider set of options for using UVC to prevent and treat infections both internally and externally for humans and animals.

One way to substantially increase the penetrating power of UVC and other forms of germicidal radiation is to administer the light in the form of very short, high intensity pulses. This form of application takes advantage of the ability of a powerful peak dose to punch through intervening tissue. It also creates a pulsed environment where parameters change rapidly, which is also detrimental to an organism trying to maintain a steady state biotic condition. The high intensity also ensures that the minimum dosage strength necessary to damage an organism is delivered while the 'off times' in between the pulses greatly decreases the amount of energy that actually is delivered thus minimizing exposure.

Example 1

To illustrate the effect on the use of high intensity pulsing to enhance penetration of tissues two devices were compared. One unit was a low pressure mercury lamp unit manufactured by American Ultraviolet, model CE-12-2H with two UV bulbs each consuming 6 watts of energy and emitting approximately 85% of their light as UV at 254 nm. See Table 1 below. This unit represented a steady state, non-pulsing source of UVC. The second device was a xenon pulsed lamp manufactured by Xenon corporation, model RC-700 capable of pulsing 120 times per second (25 µs on and 8.3 ms off). The RC-700 unit was capable of providing an average output of 1 to 5 $mw/cm^2$ of UVC at 254 nm when its intensity was averaged over a period of several seconds. While the unit emitted a low average wattage of UVC, when it was pulsing (its pulse time was 0.3% of the total time) it could emit an equivalent peak dose of between 333 to 1666 watts of UVC during the each short burst, or an equivalent of about 13 to 66 µJ of UVC at 254 nm per pulse. Note that this data is applied light energy, not input power.

Detection of UVC was accomplished using an IL1700 radiometer equipped with an SHD240 detector. This device can be used to measure peak dosages or can provide an average dosage over time. The average dosage over time was of interest in this research since the timing and the length of individual pulses of the xenon flash bulb were well documented.

The tissue used were nail clippings taken from a person who did not have nail infections. Nail clippings were used since the research was to be applied first to treatment of nail infections. However, similar results are expected from exposing skin and other tissues to these forms of germicidal light.

Five nail clippings were tested. Two plates with a ⅛-in holes were used to test the nail clippings. A reading was taken when no plates were between the lamp and the detector, another reading when the plates were in place but no nail was covering the ⅛ in hole, and one reading with the nail sandwiched between the plates to cover the ⅛-in hole. The individual data for each nail clipping are as follows:

TABLE 1

Transmissivity testing comparing Low Pressure Mercury Lamp (continuous light) and Xenon Pulsed Flash Lamp

|  | Low Pressure Mercury Lamp Meter reading | Xenon Pulsed Flash Lamp Meter reading | Notes |
|---|---|---|---|
| Nail Clipping 1 | | | |
| A. No Plate | 'Hi' | $5.0 \times 10E-5$ | |
| B. Plate with no nail | $2.0 \times 10E-4$ | $2.3 \times 10E-5$ | |
| C. Plate with nail | $1.5 \times 10E-9$ | $1.6 \times 10E-7$ | |
| D. Transmissivity (C/B) | $7.5 \times 10E-6$ | $6.9 \times 10E-13$ | Pulse lamp approximately 1000 times more effective |
| Nail Clipping 2 | | | |
| A. No Plate | 'Hi' | $4.9 \times 10E-5$ | |
| B. Plate with no nail | $1.8 \times 10E-4$ | $3.3 \times 10E-6$ | |
| C. Plate with nail | $5.6 \times 10E-10$ | $1.5 \times 10E-8$ | |
| D. Transmissivity (C/B) | $3.1 \times 10E-6$ | $4.5 \times 10E-3$ | Pulse lamp approximately 1400 times more effective |
| Nail Clipping 3 | | | |
| A. No Plate | 'Hi' | $4.8 \times 10E-5$ | |
| B. Plate with no nail | $1.3 \times 10E-4$ | $1.6 \times 10E-5$ | |
| C. Plate with nail | $1.0 \times 10E-9$ | $1.7 \times 10E-7$ | |
| D. Transmissivity (C/B) | $7.7 \times 10E-6$ | $1.1 \times 10E-2$ | Pulse lamp approximately 1400 times more effective |

TABLE 1-continued

Transmissivity testing comparing Low Pressure Mercury Lamp (continuous light) and Xenon Pulsed Flash Lamp

| | Low Pressure Mercury Lamp Meter reading | Xenon Pulsed Flash Lamp Meter reading | Notes |
|---|---|---|---|
| Nail Clipping 4 | | | |
| A. No Plate | 'Hi' | 4.9 × 10E−5 | |
| B. Plate with no nail | 9.9 × 10E−5 | 2.0 × 10E−5 | |
| C. Plate with nail | 1.0 × 10E−9 | 6.7 × 10E−8 | |
| D. Transmissivity (C/B) | 1.0 × 10E−5 | 3.4 × 10E−3 | Pulse lamp approximately 350 times more effective |
| Nail Clipping 5 | | | |
| A. No Plate | 'Hi' | 4.9 × 10E−5 | |
| B. Plate with no nail | 2.2 × 10E−4 | 2.0 × 10E−5 | |
| C. Plate with nail | 9.0 × 10E−10 | 8.2 × 10E−8 | |
| D. Transmissivity (C/B) | 4.1 × 10E−6 | 4.3 × 10E−3 | Pulse lamp approximately 1000 times more effective |

The data from testing of nail clippings indicates that a pulsed source of UVC is capable of penetrating a nail between 350 and 1400 times more effectively. On average the pulsed light was 1000 times as effective (three orders of magnitude) and capable of penetrating a nail as a low pressure mercury lamp of equivalent UVC output. Thus a dosage of light that would take one hour (3,600 seconds) to deliver underneath a nail using the American UV model CE-12-2H lamp could be delivered using a Xenon RC-700 lamp in approximately 15 seconds even though the average UVC output at 254 nm from the RC-700 is only 25% that of the American Ultraviolet lamp.

4.8 Example 2

Clinical Trials Using Germicidal Light to Treat Nail Infections

Clinical trials were conducted consisting of two prototype devices each of which was used to treat 15 subjects each (30 total). One device, labeled Prototype A, was a low pressure mercury lamp (LPML) that was capable of providing at total of 17 mw/cm$^2$ of UVC at 254 nm over the area to be treated. The second device labeled Prototype B, was a pulse xenon lamp (XPL) capable of providing pulsed full spectrum light from approximately 180 nm to more than 1600 nm. Prototype B was capable of providing a total of 3.87 mw/cm$^2$ of UVC from 240 to 280 nm over the area to be treated.

Fifteen subjects received treatment using Prototype A. Each treatment irradiated the target nail with 0.18 mw/cm$^2$ of UVC at 254 nm for 45 minutes for 4 sessions each spaced one week apart. Total dosage of UVC to the top of the nail was therefore approximately 22 J/cm$^2$ during each of the four treatments. UVC light was generated by a commercially available low pressure mercury lamp manufactured by Heraeus (model NG6062) which is used to disinfect surfaces such as food containers.

Figure 3:
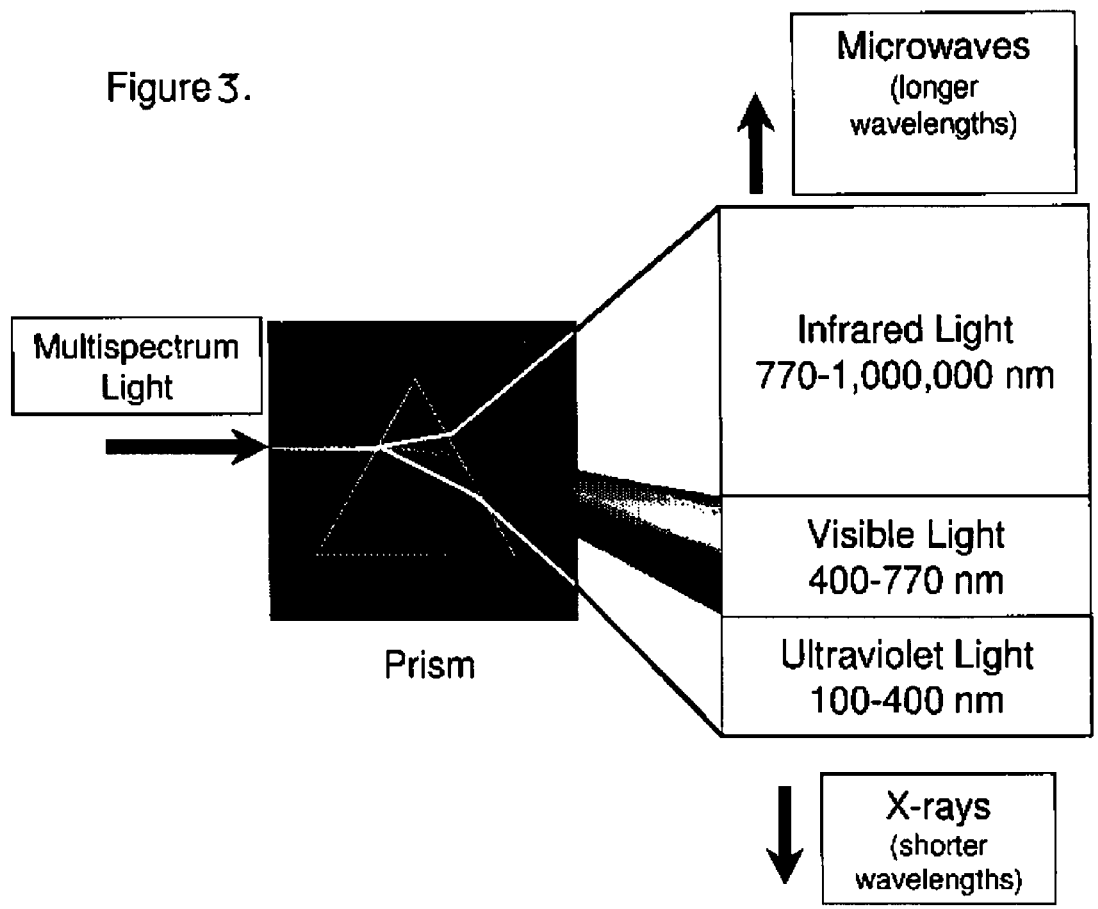
FIG. 3 is a diagrammatic view showing various bands of light.

Fifteen subjects received treatment using Prototype B. Each treatment irradiated the target nail with 3.87 mw/cm$^2$ of UVC from 240 to 280 nm for 8 minutes for 4 sessions each spaced one week apart. Total dosage of UVC to the nail was therefore approximately 1.86 J/cm$^2$ for each of the four treatments or about $1/12^{th}$ as much given using Prototype A. Light for the treatment was generated by a commercially available xenon pulsed lamp manufactured by Xenon (model RC-700) which is used to disinfect surfaces such as food containers. As opposed to the narrowband mercury lamp, the xenon lamp provide multiple wavelengths of light. In addition to the UVC wavelengths of interest, the lamp also provided the following dosages of light during each treatment lasting 8 minutes:

Far UV from 180 nm to 240 nm—0.8 J/cm$^2$
UVC from 240 nm to 280 nm—1.9 J/cm$^2$
UVB from 280 nm to 320 nm—3.8 J/cm$^2$
UVA from 320 nm to 400 nm—15 J/cm$^2$
Visible light from 400 nm to 750 nm—113 J/cm$^2$
Infrared from 750 nm to 880 nm—1.1 J/cm$^2$
Infrared above 880 nm—estimated to be about 67.5 j/cm$^2$ Note that total dosage of light in the UV range was 22 J/cm$^2$ and total light dosage (between 180 and 880 nm) was 135 J/cm2 for each of the treatments with the xenon pulsed light. See the light spectrum reference table provided in FIG. 3.

Results of Clinical Trials—Of the 15 subjects treated with Prototype A, three dropped out of the study and 12 were evaluated after 1, 2, 3, 8, and 12 weeks. Average clear new nail growth was 2.5 mm after 12 weeks with 7 of the 12 subjects having more than 2 mm of new nail growth. Subjects were also graded on the IGA (Investigator Global Assessment) scale of 0 to 5 for nail appearance with lower numbers representing clearer nails and higher numbers less translucent nails. On average, during the trials there was a 0.27 improvement on this scale (changing from 2.64 to 2.37) for patients treated with the Prototype A light.

The dosages applied by the low pressure mercury lamp and the xenon pulsed lamp were as follows:

LPML—dose to top of nail=22 j/cm$^2$, dose to skin under nail=1.4 mJ/cm$^2$, average dose to nail=11 J/cm$^2$.
XPL—dose to top of nail=1.9 j/cm$^2$, dose to skin under nail=11 mJ/cm$^2$, average dose to nail=1.0 J/cm$^2$.

It should be noted that while only $1/11^{th}$ as much UVC was applied using the XPL approximately 8 times more UVC penetrated the nail to the skin the was under the nail. The average dosage of UVC applied to the cross-section of the nail was also 11 times higher using the LPML. For the clinical trials it was felt that the much higher overall dose would offset it's the LPML lower penetrating ability and that both sets of subject would have similar results.

Of the 15 subjects treated with Prototype B, two dropped out of the study and 13 were evaluated after 1, 2, 3, 8, and 12 weeks. Average clear new nail growth was 2.5 mm after 12 weeks with 8 of the 13 subjects having more than 2 mm of new nail growth. Subjects were also graded on the IGA (Investigator Global Assessment) scale of 0 to 5 for nail appearance. On average there was a 0.69 improvement on this scale (changing from 2.64 to 2.35).

The data indicate that both devices were capable of efficaciously treating the infection to so that new nail growth would be clear. Additionally, however, it was noted that the broad spectrum xenon pulsed light was also capable of providing improvement in the appearance of the nail.

It appears, therefore, that UVC applied to nails with a low pressure mercury lamp is able to inactivate organisms that cause nail infections and clear the infection. It also appears that pulsed, broad spectrum germicidal light is even more efficacious in curing nail infections. This occurred even though the UVC dose of the pulsed light was less than 10% of that delivered by the low pressure mercury lamp. Thus, while treatment with UVC alone successfully treated nail infections, treatment with broad spectrum light pulsed germicidal light had the unexpected result of being more efficacious at much lower doses.

It should be noted that although the clinical trials focused on nail infections, the results can be applied to the treatment of skin and other tissues of the body. Enhancement of the delivery of germicidal light (by pulsing, using wide spectrum light, and/or by other modifications) can significantly improve the efficacy of treatment and result in a lower overall dose required.

4.9 Discussion of Research Results Using Pulsed Lamp Technology

As demonstrated in Example 2, results from lab research on the use of short, high intensity pulses indicate that pulsing can increase transmissivity through the nails by approximately 3 orders of magnitude (1000 times). The increase in transmissivity does not take into account the added synergistic germicidal effects that may be obtained from using a wide band polychromatic light source. Thus, it is possible to enhance the delivery of germicidal light by several orders of magnitude to make it more effective to prevent and treat infections.

Clinical trials conducted on nail infections verify that wide band pulsed germicidal light can be used to enhance the treatment of undesirable tissue and cells and can do so at a much lower dose than a comparable dose of UVC delivered by a narrowband continuous light source.

One of the implications of this research is that lamps of much lower power could be pulsed to greatly enhance their efficacy. One possible source of light that becomes much more attractive because of this discovery is the use of UV emitting LEDs. In the last several years LEDs have been developed that can emit light in the UVC range. These LEDs have begun to be used in germicidal applications such as the disinfection of air and water. However, they would not be as attractive to prevent and treat infections due to their low power, which has been thought to greatly decrease their ability to penetrate and deliver the required dose. If LEDs emitting UVC were pulsed correctly, such as through the use of selective filters, shields, mirrors, regulators or modulators, the LED lights have great potential to treat infections.

In addition, there are a wide variety of excimer lamps that emit light in the UVC range that can be pulsed to increase their efficacy. For example xenon-iodine (XeI, also designated as XeJ) excimer lamps emits most of its light at 253 nm. Additionally chlorine (Cl—Cl) excimer lamps emit at 258 nm and xenon-bromine (XeBr) emit at 283 nm. While the latter emission is just outside the UVC range it still has the potential to be very germicidal. Pulsing of these lamps could greatly increase their efficacy in treating infections. The ability of these lamps to deliver one or several high energy pulses that are precisely targeted also makes them ideal for use as a preventative application. For example, those prone to nail infections may have a preventative dose applied during periodic visits to a podiatrist.

Additionally, it is possible to modify the current of a pulsed polychromatic light source such as a Xenon pulsed lamp by applying a higher current to it to force more of its light to be emitted in the UVC range. Table 2 below illustrates the difference between low current and high current operation.

TABLE 2

Xenon Flash Lamp Approximate energy distribution for Hi and Lo current operation

| Wavelength | High Current Operation | | | Low Current Operation | | |
|---|---|---|---|---|---|---|
| | Intensity | Percent | Wavelength | Intensity | Percent |
| 200 | 0.25 | 3.25% | 200 | 0.18 | 2.14% |
| 250 | 0.75 | 9.74% | 250 | 0.27 | 3.21% |
| 300 | 0.55 | 7.14% | 300 | 0.35 | 4.16% |
| 350 | 0.5 | 6.49% | 350 | 0.45 | 5.35% |
| 400 | 0.65 | 8.44% | 400 | 0.45 | 5.35% |
| 450 | 0.7 | 9.09% | 450 | 0.53 | 6.30% |
| 500 | 0.7 | 9.09% | 500 | 0.58 | 6.90% |
| 550 | 0.65 | 8.44% | 550 | 0.5 | 5.95% |
| 600 | 0.42 | 5.45% | 600 | 0.5 | 5.95% |
| 650 | 0.33 | 4.29% | 650 | 0.45 | 5.35% |
| 700 | 0.32 | 4.16% | 700 | 0.4 | 4.76% |
| 750 | 0.28 | 3.64% | 750 | 0.4 | 4.76% |
| 800 | 0.32 | 4.16% | 800 | 0.35 | 4.16% |
| 850 | 0.35 | 4.55% | 850 | 0.6 | 7.13% |
| 900 | 0.3 | 3.90% | 900 | 0.7 | 8.32% |
| 950 | 0.25 | 3.25% | 950 | 0.6 | 7.13% |
| 1000 | 0.2 | 2.60% | 1000 | 0.6 | 7.13% |
| 1050 | 0.1 | 1.30% | 1050 | 0.3 | 3.57% |
| 1100 | 0.08 | 1.04% | 1100 | 0.2 | 2.38% |
| Total | 7.7 | 100.00% | Total | 8.41 | 100.00% |

Comparison of Low and High Current Operation
High current operation has three times the UVC output of low current operation per applied Joule
High current operation has about two times the UVB output of low current operation per applied Joule 4.10 Undesirable Wavelengths of Polychromatic Light and Methods to Mitigate Problems "Polychromatic light" refers to a wide range of light. In some embodiments, polychromatic light can be provided by a xenon flash lamp. Some wavelengths in polychromatic light are undesirable due to their side affects. For example UVB in even low doses can cause sunburn and has also been shown to be carcinogenic. This is one of the reasons that polychromatic light has not been used on humans or animals. However, it is possible to use filters to reduce or totally eliminate undesirable wavelengths of light. This can be accomplished by a variety of means such, for example, as the use of notch filters (that exclude only a very specific band of light), mirrors that preferentially reflect certain wavelengths of light but absorb unwanted bandwidths, or thin films applied over optically transparent materials to filter out undesirable bandwidths. This is not an exhaustive list but is illustrative of types of filtering that one skilled in the art could use to screen out undesirable light. The present invention is not limited to a specific type of filter. The type of filter described above has not been used in the past since the filtering technology has only been used in a variety fields that are not health related and those skilled in the art of treating infections have not thought apply it in this field. Additionally, filters of this type can be prohibitively expensive. However, this novel combination of technologies greatly enhances the use of polychromatic light applied to tissues to inactivate undesirable cells or organisms. From table 1 above it appears that average transmission of UVC through the nail using a low pressure mercury lamp is approximately 6.5E-06 while the average transmission using a xenon pulse lamp is 6.0E-03 which indicates that the pulsed light has about 1000 times the ability to penetrate nails 4.11 Use of Synergistic and Other Germicidal Wavelengths to Enhance Treatment Other wavelengths can also act germicidally besides the UVC band and are discussed in detail in U.S. application Ser. No. 11/154,707, filed Jun. 17, 2005 which is incorporated by reference into this application. An example of these wavelengths is illustrated by recent experiment data conducted in March and April of 2007 which included a semi-quantitative evaluation of whether there are other germicidal wavelengths generated by a low pressure mercury amalgam lamp. Bakers Yeast was used as the indicator organism since it is easy to culture. One-quarter teaspoon of bakers yeast was mixed in one-quarter cup of warm water and fully dissolved. One ml of solution was put in each of 6 small sterile containers. Each container was irradiated as follows:

1A—fully covered, no UV light
2A—Irradiated with UV light for 5 minutes, no filter used
3A—Irradiated with UV light for 5 minutes, a 275 nm bandpass filter was used (only light above 275 nm reached the yeast)
4A—Irradiated with UV light for 5 minutes, a 325 nm bandpass filter was used (only light above 325 nm reached the yeast)
5A—Irradiated with UV light for 5 minutes, a 425 nm bandpass filter was used (only light above 425 nm reached the yeast)
6A—fully covered, no UV light. However, the water used to dilute the yeast was combined with approximately 10 grams of nail clippings that had been irradiated by UV light for 5 minutes. This was done to determine if the UV light possibly changed the nail so that it had a substance toxic to the yeast which would then retard its growth.

Once these samples were exposed, six more samples identical to above were prepared and irradiated. These were labeled 1B, 2B, 3B, 4B, 5B, and 6B respectively.

The yeast was then transferred to individual Millipore Yeast culture tubes and incubated for 72 hours. There was no growth observed after 72 hours so the tubes were left for an additional week in ambient conditions. The following results were observed after 10 days total time (72 hours plus 7 days):

1A and 1B—6 and 2 colonies—ave. 4 colonies
2A and 2B—1 and 1 colonies—ave. 1 colonies
3A and 3B—3 and 1 colonies—ave. 2 colonies
4A and 4B—2 and 2 colonies—ave. 2 colonies
5A and 5B—5 and 5 colonies—ave. 5 colonies
6A and 6B—5 and 3 colonies—ave. 4 colonies The colonies were small white and fluffy to the naked eye. The were about 1 grid in diameter for the most part.

The data indicates several findings. One is that using water that irradiated nails have been soaked does not effect growth. Second is that UV at 254 nm is effective in inactivating yeast. Third is that wavelengths generated by a mercury lamp above 425 nm has little germicidal effect. Finally, since the sample irradiated with a 275 nm and a 325 nm bandpass filter have similar inactivation (about half that of the sample with no filters). This indicates that the germicidal light is in the range of 325 nm to 425 nm (since if it was between 275 to 325 nm there would be a difference in the two samples growth). In the range of 325 nm to 425 nm there are only two wavelength generated by the low pressure mercury lamp that have any magnitude—they are at 365 nm (1.7% of the amount of 254 nm light generated) and 405 nm (2.0% of the amount of 254 nm light generated). Therefore, it appears that one or both of these wavelengths have germicidal characteristics with respect to yeast and most probably other organisms. Additionally, since these wavelengths are longer than UVC wavelengths they can penetrate better and therefore are a useful adjunct to UVC therapy. Therefore, these two discrete wavelengths are among those also claimed as germicidal and synergistic wavelengths that can be used to treat skin and nail infections, tumors, wounds, psoriasis, etc.

4.12 Mechanisms of Destruction Using Pulsed Light

Although the Applicant does not wish to be bound by any theory of operation a description of how pulsed light is efficacious is provided herein for illustrative purposes. Since there are many ways pulsed light can be said to be efficacious this description should not be taken as exhaustive or definitive but only exemplary.

It UVC range is germicidal since it is the band that most readily damages the genetic material of an organism and prevents it from reproducing. Although UVC in low doses can inactivate an organism substantially by damaging its genetic material, application of UVC in higher doses can also damage other cellular structures and even kill the cell or organism if enough light is applied. Additionally, even very low doses of UVC can damage an organism or cell enough that it goes into apoptosis, a form of programmed cell death.

Pulsing light can enhance the proportion of UV in light relative to the rest of the spectrum. For example, as noted in this application pulsing of a Xenon lamp can more than double the amount of UV light below 300 nm compared with a continuous xenon or a weakly pulsed xenon lamp. Roughly speaking, the more voltage that is applied per pulse the more UV there is in proportion to the rest of the spectrum. Thus, very high voltage pulsing of xenon is a preferred way to increase UV output of a lamp.

Additionally, pulsing light can prove more efficacious since it hinders a cell or organism from equilibrating to static conditions. The continuous change of state will not only stress an organism it will also fatigue the organism and slow its response time. Very short pulsing of light can also penetrate so quickly that an organism or cell cannot mount proper defenses.

Pulsed light also creates a much higher point input of energy, which is far more difficult for a cell or organism to disperse that a lower, steady input of light. By applying very short, intense pulses it is possible to apply peak energies that are a million times or more stronger in their peak than the same amount of light applied on a continuous basis. This intense energy can totally destroy critical structures in an organism or cell, which will prevent it from maintaining viability.

The use of wide band pulsed light has the advantage of overwhelming the cell with multiple light waves that can cause damage to various structures for the organism or cell. For example, the UVC range can damage the genetic material of the cell while the UVB or UVA band damages the membrane of the cell or organism. Other bands may be absorbed by other structures such as mitochondria. Thus, while UVC may do the primary damage to a cell, the other wavelengths act synergistically to inactivate the cell by killing it or by damaging its ability to reproduce.

UVC is about the shortest wavelength of light. Use of wideband pulsed has longer wavelength and will thus enhance the penetration of the light through tissue. Additionally, research indicates that the penetration of UV is also enhanced by the inclusion of other wavebands. Thus, the inclusion of wideband light not only acts synergistically to inactivate organisms and cells, it also acts synergistically to help UV penetrate better.

4.12.1 Wide Spectrum Germicidal Light

Wide spectrum light has germicidal properties and offers some advantages to the use of narrowband UV light. These advantages include the following:

a. Although the UV component of polychromatic light still does not penetrate well, other wavelengths can penetrate better and thus contribute relatively more than usual to inactivating organisms. Thus, polychromatic radiation has the potential to inactivate organisms using less UVC than the use of UVC light alone b. Multiple wavelengths of light can acts on various processes of the cells and cause inactivation of organisms at lower energies than ultraviolet light itself. In addition to greater inactivation of organisms using polychromatic light, the inactivation of a wider variety of organisms is possible since the multiple bands of lights affect each type of organism differently and will thus affect a wider variety of organisms.

c. Different wavelengths are absorbed by different part of each organism thus use of multiple wavelengths increases the chance that structures that are essential to the organism will be inactivated thus rendering the organism harmless.

Wideband UVC light, defined at light that covers the entire UVC spectrum of 240 nm to 280 nm as opposed to monochromatic UVC light that emits primarily at one wavelength (such as 254 nm for a low pressure mercury lamp), also has germicidal properties and offers advantages to the use of narrowband UV light. These advantages include the following:

a. Since all of the UVC range exhibits strong germicidal properties it is possible to spread the dosage over the entire band, which thus limits the amount that is delivered at any one bandwidth. This may act to alleviate any negative responses to the UV (such as erythema).

b. While the optimal range of UVC for inactivation of organisms due to the formation of pyrimidine dimers is at about 258 nm, research indicates that various organisms are more affected at other ranges of the UVC spectrum. Use of broad band UVC between 240 nm and 280 nm ensures that energy is delivered at wavelengths that all organisms are susceptible to.

Pulsed light variants of polychromatic and UVC light also have germicidal properties and offers advantages to the use of narrowband UV light. These advantages include the following:

a. Laboratory data shows that high intensity pulses are significantly more effective at penetrating tissue than when the same amount of light energy is uniformly applied over a longer period of time. Other research indicates that pulsing of high energy light can increase the depth of penetration through tissues by several orders of magnitude. This finding, which is not common knowledge to those skilled in the art of treating skin and other body disorders, permits the novel use of pulsed light to inactivate organisms at a much lower dose of UVC than continuously emitting light.

b. Since pulsed light can be more effectively used to penetrate tissue and inactivate organisms it can substantially reduce the time necessary for treatment.

c. Since pulsed light can be used to more effectively used to penetrate tissue it can be used to treat infections that are substantially deeper than surface infections.

d. Pulsed light emits significantly higher energy in a very short time period compared with continuous light. These short, high intensity pulses appear to overwhelm cells and damage vital components, which are unable to dissipate the excess instantaneous energy being applied. Additionally, short pulses of light with longer periods of low or no light permit time for energy to dissipate and thus limits the amount of heat that surrounding tissues may experience which also limits collateral damage e. The very high peak of the energy pulse is often several orders of magnitude greater than the average energy applied. This high peak dose is more likely to exceed the threshold energy (also called the energy of activation) that would drive reactions that do not begin until this threshold is reached. Thus, these peak doses can trigger reactions that will contribute to the inactivation of organisms by damaging vital components or forming compounds that are antibiotic in nature such as singlet oxygen or ozone.

f. Pulsed light can damage undesirable cells with a lower overall dose since it can deliver extremely high doses that overwhelm the cell in short pulses with substantial periods between each pulse. Thus an organism might experience a peak of several orders of magnitude greater than if the light were uniformly spread over time.

Coherent light variants of polychromatic and UVC light such as lasers also have germicidal properties and offers advantages to the use of narrowband UV light. These advantages include the following:

a. Lasers can be pulsed to offer the same advantages that other pulsed light sources possess, namely they can penetrate better than continuous light.

b. All lasers make use of coherent light of a very narrow band, which can thus be tuned to do the most damage to infectious organisms while not affecting other organisms as greatly. For example, if a particular organism is best deactivated at a wavelength of 245 nm, a tunable laser could be used to deliver light precisely at that wavelength. Surrounding tissue and organisms would not be as greatly affected since most organisms are affected most strongly between 258 nm and 262 nm.

4.12.2 Pulsed Polychromatic Light Dose Sufficient to Inactivate Microbes

While most wavelengths of light are not germicidal by themselves, they can act synergistically to inactivate an organism. When combined with the germicidal ability of UVC light, multichromatic sources can often lower the required dose of UVC by up to an order of magnitude or more. Xenon flash lamps are a particularly attractive source because in addition to multiple wavelengths of light they can be pulsed to provide extremely high momentary doses of light and this light can be delivered repeatedly via a strobe mode. This can allow for greater applied light dosage ("germicidal light at the source of the infection") per amount of generated light ("germicidal or other light as measured at the light source"). This has the following advantages:

a. High peak doses—very high peak doses can be delivered using high energy pulses that have short durations. The overall energy applied can still be lower on average than applied by a continuous lamp, however, the peak doses could be 10 to 1,000,000 times or more than the average dose.

b. The high peak doses can act as a 'punch' to cause damage that might not be accomplished at lower energies. An analogy would be applying pressure to drive a nail through a piece of wood. If a person pushed on a nail with his hand for days he may not be able to drive a nail through wood. However, a strong momentary blow to the nail delivered via a hammer can drive the nail quickly. The total amount of energy applied by hand to the nail could actually be greater but the momentary energy application via a hammer is more likely to successfully drive the nail. In the same way high peak doses have the ability to damage the genetic material quickly and effectively without the use of high average doses. Recent laboratory data indicate that the high energy pulsed strobing of light can increase its ability to penetrate tissue by several orders of magnitude.

c. Repetitive pulsating doses—a lamp that is pulsed, or strobed, can deliver over one hundred intense pulses per second. These pulses have the effect of rapidly changing the environment of the organism and also affecting its biological processes. The repetitive fluctuations can do damage that continuous light might not accomplish. An example would be the flexing of a piece of metal. While it might flex once or every a dozen times without breaking, continuous flexing of a piece of metal will cause it to fatigue and eventually break. With pulsed light, the strobing of light at multiple pulses per second can effect this type of fatigue and failure in an organism in a short period of time. The strobing may also create harmonic waves which do additional damage to the cellular processes of the organism.

d. Pulsing with very high voltage can shift the spectra of the light to shorter wavelengths and dramatically increase the amount of light emitted in the UV range which is also the wavelength that is most germicidal.

4.13 Illustrations of Device to Prevent and Treat Skin and Nail Infections

Figure 4:
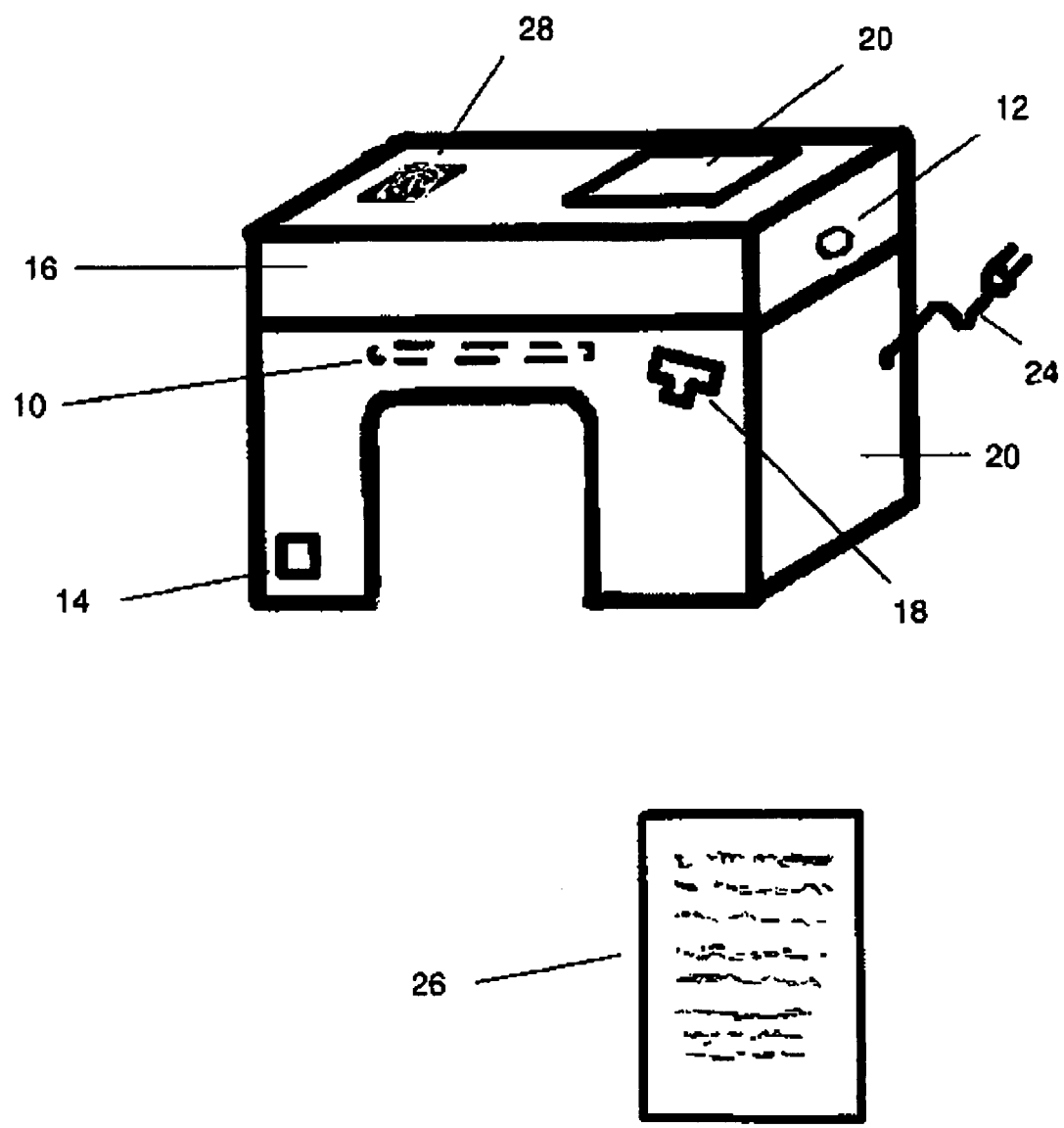
FIG. 4 is a diagrammatic view of a light device according to a preferred embodiment of the present invention for use in treating skin or nail.

FIG. 4 illustrates a device to prevent and treat skin and nail infections. The device may have any combination of the following components:

Light Source (10) that can be tuned to a specified spectral output or a fixed spectral output.

A timer (12)

A means (14) to determine the intensity of the light

A processing unit (16) that can perform calculations, store data, track usage, troubleshoot problems, etc.

A camera (18) to take pictures

A shield (20) to prevent light from illuminating other areas

Safety Labels (22)

Ground fault protector (24)

Safe Operating Instructions (26)

Security devices (28)

A connection (30) for special attachments

Figure 5:
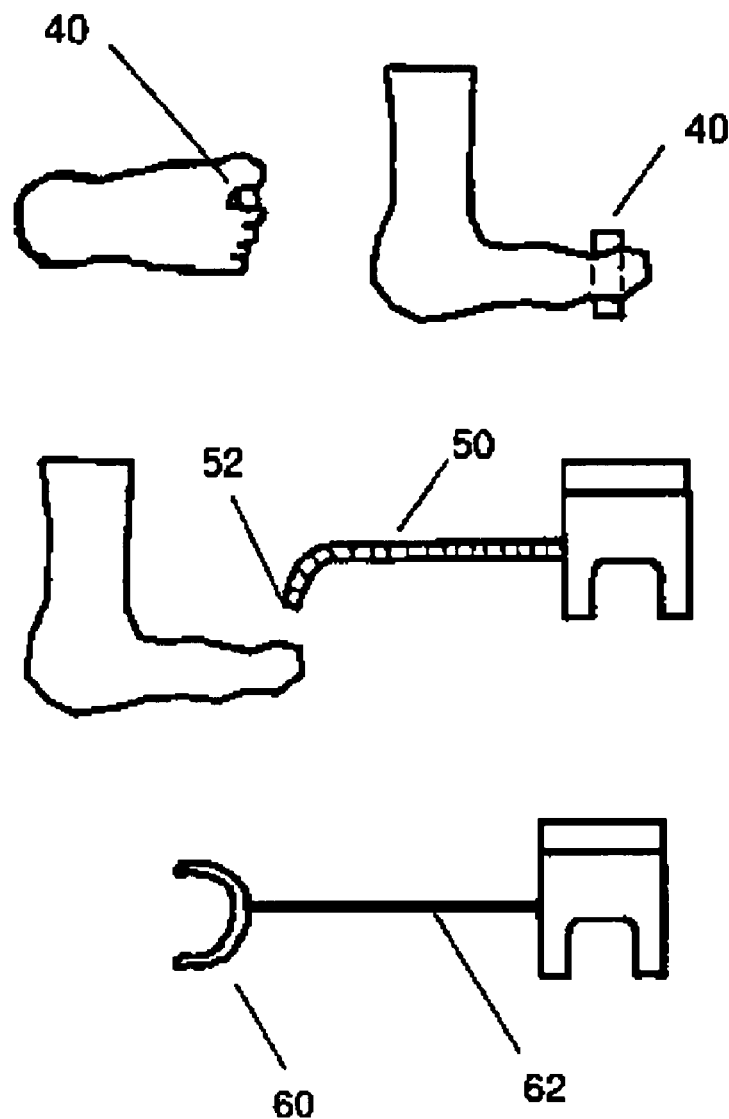
FIG. 5 is a diagrammatic view of a light device accessories according to a preferred embodiment of the present invention for use in treating skin or nail.

FIG. 5 illustrates some of the special attachments that could be used for treatment and includes the following:

a. An attachment (40) that can provide light to hard to reach areas such as those between the toes.

b. An attachment that transmits light via a flexible cable (50) and delivers this light at the end of the cable (52) to treat a specific area.

c. An attachment that can be inserted in the mouth (60) and can receive light from a flexible cable (62) that can transmit such light.

5 PREFERRED METHODS OF USE OF INVENTION

As demonstrated in U.S. Pat. No. 6,960,201 (Cumbie), germicidal light penetrates nails and inactivates organisms to successfully cure infections.

It has been shown that germicidal light can also be used to kill organisms and successfully treat skin and other tissue infections in parent application Ser. No. 11/154,707, filed on Jun. 18, 2005. The '707 application also details a wide variety of germicidal light that can be used to kill and inactivate organisms which can also be used to inactivate and kill undesirable cells also. The '707 application further details methods to enhance the penetration and efficacy of germicidal light.

Additionally, although polychromatic light has been used to purify food and water, it requires a significant amount of light in the UVB range, which would make it much less desirable to use on living humans or animals since even low doses of UVB will cause sunburns. However, advances in thin films and other filtering technology have not been considered by those skilled in the art of purifying food and water can for filtering out UVB. The novel combination of broad band, polychromatic light with filtering of skin-damaging wavelengths permits the use of much higher doses of polychromatic light (that has been filtered to remove UVB) than have been previously contemplated. It should be noted that thin films that are applied to optically transparent material and other types of filters can be tuned so that they filter out any range of light that is deemed undesirable. For example, it may be desirable to filter out infrared and other wavelengths to decrease the heat generated during treatment. Thus, light can be precisely tuned to have maximum effectiveness while minimizing undesirable side effects from unwanted wavelengths of light.

Light can also be channeled by a variety of devices to very specific application points. Light channels such as fiber optics that are capable of transmitting light in the UV range can be used to deliver UV light or polychromatic light that is rich in UV to specific sites such as the insides of body cavities such as the mouth, the esophagus, the lungs, stomach, anus, ears, etc. These light channels can also be used to deliver light to internal parts of the body such in a similar manner that a catheter can be used to pierce an organ or tumor. Additionally, the light channels themselves could be used as observation ports in addition to being used to deliver light to the selected target area.

Germicidal light can also be used similarly for the treatment of animals with various disorders. This could be done for both domesticated animals and others. In particular, animals that have diseases of nails or hooves and animals that have similar disorders to humans would great benefit from this type of treatment.

Germicidal light can also be used for organs that will be transplanted. Use of this light for organs will reduce the chance for infection and also the chance for rejection by the body. The inactivation of surface cells and organisms makes the possible rejection by the recipient body much less probable. In some embodiments, the germicidal light can be applied before removal of the organ from an organ donor. In some embodiments, the germicidal light can be applied after removal of the organ from an organ donor, but before inserting into an organ recipient. In some embodiments, the germicidal light can be applied after insertion into an organ recipient.

Germicidal light can be used to kill and inactivate organisms that cause disease, infections, and disorders in a similar manner. Examples of these categories includes warts, boils, strep infections, athlete's feet, eczema, cold sores, etc. These examples are not intended to be comprehensive but are only illustrative of how one skilled in the art such as a dermatologist could successfully apply this invention.

Germicidal light can be used to inactivate and kill undesirable cells by applying such light to the area or volume to be treated. Areas that are outside the targeted treatment area should be shielded from the light being used in treatment to prevent damage to healthy, desirable cells.

Germicidal light can best be used when the characteristics of the area to be treated are known with relation to the kind of light being treated. For example, if it is known that germicidal light at 254 nm can penetrate fair skin with an infection up to 1 mm when applied at a strength of 25 mw/cm2 for 10 minutes then this light can be used to treat superficial skin infections. However, if a cancerous tumor with a depth of 5 mm is to be treated it may be necessary to use a germicidal light source that can penetrate more deeply. For example, it may be best to use a 100 nanosecond pulse of polychromatic light that is rich in UVC and is generated by a xenon pulse lamp if it is known that this kind of germicidal light can penetrate a cancerous tumor to a depth of 5 mm effectively.

5.1 Treatment of Cancer

Research by Silvano Nocentini (*Apoptic Response of Malignant Rhabdoid Tumors Cells*, published in 2003 in Cancer Cell International) notes that apoptosis can be induced in malignant rhabdoid tumor cells with doses of UVC as low as 20 J/m2 (2 mj/cm$^2$), which is similar to the dose that can inactivate many disease causing organisms. It is likely that other types of cancerous cells have a similar propensity to initiate apoptosis at similar dosages given the common characteristics that these types of cells share such as similar membrane thicknesses and genetic material. However, these findings and others like them have not stimulated the development of treatments for cancer based on using UVC and other germicidal light since it is believed it cannot penetrate deeply enough. Additionally, the paradigm shift required use something potentially carcinogenic itself to cure cancer has also prevented its application. These impediments to developing an effective cancer treatment have been discussed in other places in this application. It is enough to say here though that such light can be used successfully. It is recommended that one or more of the following preferred procedures be implemented to successfully treat cancer:

a. determine what dosage is necessary to inactivate the cell that is undesirable;
b. determine the depth the light must penetrate to reach all cells that are to be treated;
c. determine how much the light used for treatment will attenuate for said light to penetrate to the necessary depth;
d. determine the most appropriate type of light for said treatment with continuous UVC light for more shallow treatments and wide spectrum pulsed light for deeper treatments;
e. determine the necessary dose of light to apply taking into account the above factors and adding a factor of safety to the calculations; and/or
f. apply the necessary dose of light to treat the cells.

For example, if it was desired to treat a melanoma skin cancer tumor that was 1 mm deep it would be possible to use a continuous UVC light therapy, however, a wide spectrum pulsed light would be preferable due to its ability to penetrate more deeply. If the melanoma tumor would initiate a apoptosis at a UVC dose of 2 mJ/cm$^2$ of wide spectrum germicidal light it would still be preferable to use the wide spectrum light due to its ability to penetrate better and because such light is generally well tolerated. If 0.1% the wide spectrum light could penetrate to the bottom of the tumor the necessary dose would be 2,000 mj/cm$^2$ (2 J/cm$^2$). However, this high dose of UVC can be well tolerated particularly if the light is pulsed and it should be noted that the surrounding skin will be fully covered ("shielded") so only the undesirable cells will be exposed to this magnitude of light. To apply this light, a practitioner could use a xenon flash bulb capable of discharging 0.1 mj/cm$^2$ of UVC per flash. This would thus require 20,000 flashes to treat the area. If lamp emitted 50 flashes per second the total treatment time would be 400 seconds or 6 minutes and 40 seconds total. Adding a factor of safety of 50% would bring total treatment time to 600 seconds or 10 minutes total.

It should also be noted that in the above example, a very high amount of UVB would also be present and applied. If only the tumor was exposed and no surrounding skin was exposed it would not be necessary to filter out the UVB and the UVB might have actually have a synergistic effect and increase the efficacy of the treatment. However, if a large amount of surrounding skin were exposed, it might be advisable to filter out the UVB light to prevent a painful reaction and possible blistering.

5.2 Treatment of Psoriasis 5.2.1 Summary of Psoriasis

Psoriasis is an autoimmune disease of the skin which affects 2% to 3% of the population worldwide. According to the National Institute of Health, between 5.8 and 7.5 million Americans are affected by psoriasis. Americans spend between $2 to $3 billion each year to treat psoriasis according to the National Psoriasis Foundation.

There are five types of psoriasis—plaque, guttate, inverse, pustular, and erythrodermic. Plaque is the most common form of the disease and appears as raised, red patches or lesions covered with a silvery white buildup of dead skin cells, called scale. About 80% of those affected have plaque psoriasis. Guttate appears as small red spots on the skin. Inverse occurs in armpits, groin and skin folds. Pustular manifests as white blisters surrounded by red skin. And erythrodermic has intense redness over large areas.

Research indicates that psoriasis is an immune-mediated condition. This means the condition is caused by faulty signals in the body's immune system. It is believed that psoriasis develops when the immune system tells the body to over-react and accelerate the growth of skin cells. Normally, skin cells mature and are shed from the skin's surface every 28 to 30 days. When psoriasis develops, the skin cells mature in 3 to 6 days and move to the skin surface. Instead of being shed, the skin cells pile up, causing the visible lesions.

Psoriasis cases are classified as mild (less than 2% of the body's surface area affected and usually localized on the knees, elbows, scalp, hands and feet), moderate (between 2% and 10% coverage usually appearing on the arms, legs, torso and head), and severe (greater than 10% coverage and potentially involving all areas of the skin). Even a small amount of body cover such as 2% can be significant if that area is especially sensitive such as the hands or feet. An estimated 80-85% of psoriasis cases are mild to moderate. Psoriasis is rarely life-threatening, however, a person's quality of life can be seriously degraded. Additionally, there is a high economic cost to both individuals and the country since it causes an estimated 56 million loss work hours each year.

Dermatologist us the PASI scale (Psoriasis Area and Severity Index) to determine the severity of the disorder in individuals. PASI is a composite measure of erythema (redness), induration (plaque thickness), and desqamation (scaliness). The scale ranges from 0 (clear) to 72 and is calculated for an affected area and then multiplied by the amount of coverage on a individual. Clinicians and practice dermatologists often devise their own "modified PASI," a scoring system that best meets their descriptive needs, and clinical papers always describe how a particular trial's PASI is calculated. For instance, while a patient may have only 2% coverage, if it is on the feet and the patient cannot walk, a physician would score this condition higher than a non-debilitating similar-sized plaque on the trunk area. The percent decrease in PASI score is the commonly accepted measure of the efficacy of psoriasis treatments, with a 75 percent decrease in PASI score (PASI 75) viewed as a clinically significant outcome.

Psoriasis can be treated with topical medications, oral medications, and/or with phototherapy. There are hundreds of over-the-counter topical medications that are used, however, these cannot be used continuously and provide at most temporary relief. Treatment with steroids is more powerful and effective. However, use of steroids is expensive and their use must be carefully monitored and applied. If steroid therapy is abruptly stopped, it can cause severe problems which can be life threatening. Long-term steroid use can lead to tachyphylaxis—loss of effectiveness. As steroids pass into the blood stream, systemic side effects can include high blood pressure, cataracts, glaucoma, hypothamic-pituitary-adrenal axis suppression, manifestations of Cushing's Syndrome, diabetes, and growth of body hair on women. While not conclusively proven, there is concern that long-term corticosteroid use may hasten the onset and severity of osteoporosis.

Non-steroidal topicals such as vitamin D analogs were introduced to the U.S. market in the early 1990s. Vitamin D analogs inhibit proliferation of skin cells and act to reduce inflammation. Clinical data for the treatment of mild to moderate chronic plaque psoriasis showed a mean difference in the percentage change in PASI score of 44%, similar to Class 2 steroids, but it may take two months to achieve this benefit, not the several weeks for steroids. Non-steroidal topicals do not have the serious side effects associated with steroids.

Systemic agents include antimetabolite drugs (methotrexate) and immunosuppressives (cyclosporine). Systemic drugs are used for the more severe forms of psoriasis and show good results—70% to 80% of patients show 75% improvement and clearing is frequent; however, their toxicity limits their usage. Cyclosporine is a powerful immunosuppressant whose major application is in organ transplantation to prevent rejection of a transplanted organ by the body's immune system. While highly effective, cyclosporine has a broad range of systemic side effects that may involve the gastrointestinal system, the kidneys, lungs, musculoskeletal system, reproductive system and increases risk of lymphoma and other cancers.

In addition to the above treatments, UVA and UVB phototherapy is also widely used to treat psoriasis. Plaque psoriasis responds positively to UV light and exposure to sunlight has long been known to be therapeutic. There are two frequency spectra of UV that penetrate the atmosphere: UVB from 290 to 320 nanometers (nm) and the longer frequency UVA—320 to 400-nm. So-called "broad band" UV therapy was developed at the Mayo Clinic in the 1920s, the start of light booth therapy where UV-emitting bulbs are arrayed in a booth in which the patient stands. Phototherapy has since been refined into two categories.

UVA: The longer waves of UVA penetrate the skin more deeply than UVB and require a photosensitizing agent to be effective in treating psoriasis, psoralen, a drug usually taken orally, but can be applied topically or by immersion. Psoralen+UVA=PUVA. The combined photosensitizer and UVA energy inhibit DNA synthesis in skin cells and suppress the skin cell proliferation of psoriasis. Treatments are repeated two or three times a week and it takes about 30 to 40 treatments for full effect. Once the psoriasis has improved about 95%, the patient starts weekly treatments which gradually become less frequent until they are administered only for flare ups.

For moderate to severe patients PUVA is generally very effective, typically an 85% decrease in PASI is achieved, and once a patient reaches remission results are long lasting, roughly six months or longer. However, as psoralen also affects the retina, patients are highly sensitive to light for hours after the drug is taken, use of wrap-around sunglasses for 24 hours post-treatment is recommended, and additional side effects can include nausea (common), itching, and increased risk of cataracts. White spots commonly develop where psoriasis plaques had occurred, particularly in people with naturally darker skin. A longer term risk stems from the fact UVA penetrates the skin more deeply than UVB, so there is a greater danger of deep skin damage and accelerated skin aging. It has been known for some time that PUVA can modify DNA and cause genetic mutations. PUVA is known to increase the risk for squamous cell skin cancer and slightly increase the risk for basal cell skin cancer, both of which, however, are nearly always curable. There is increasing concern of the long term increased risk of melanoma, a serious cancer, particularly in people who receive more than 250 treatments. Those favoring continued use of PUVA argue that it is a most effective treatment for severe psoriasis, the alternatives are usually very powerful drugs which have even more serious side effects.

Much research has concentrated on the so-called antipsoriatic range which lies between 300 to 313-nm. Therefore, most UVB treatments for psoriasis concentrate their output in the 300-313-nm range (also called narrow band UVB). In the late 1980s, Philips developed the "narrow band" TL-1 UVB bulb with a frequency output curve that peaks at 312-nm and delivers 73% of its energy into the antipsoriatic range with fairly tight distribution "tails." Erythema (sun burning) is caused by low-end UVB frequencies peaking at 295-nm and erythema is associated with mutagenic cellular response. Since NB-UVB packs most of its energy into the antipsoriatic range, fewer treatments are required than broadband UVB and PUVA to achieve remission. On the negative side, NB-UVB remission times are not as long as PUVA. An examination of the literature by MDs John Koo and Mark Lebwohl published in 1999 showed 42% of PUVA patients who maintained their maintenance regimen were still clear after one year whereas 83% of UVB patients relapsed by 6 months, relapse being defined as recurrence of 3% or more of body surface area of psoriasis than when the patient was clear. This study also noted maintenance UVB at least once a week cut the relapse rate to half.

5.2.2 Use of Germicidal Light to Treat Psoriasis

As noted earlier, psoriasis is a condition where the body produces an overabundance of skin cells that quickly migrate to the skin's surface. It is believed that this disorder is an autoimmune reaction and that it is mediated by T cells. Additionally, the basal cells in the epidermis produce an overabundance of keratinocytes (immature skin cells) which in turn produce a large amount of keratin, which is a tough fibrous protein that help form hair, skin, and nails. In normal cell growth, keratinocytes mature and migrate from the bottom (basal) layer to the surface and are shed unobtrusively over a period of about a month. In psoriasis the keratinocytes proliferate very rapidly and travel from the basal layer to the surface in only about four days. Because the skin cannot shed these cells quickly enough they accumulate in thick, dry patches, or plaques. Another important change occurs in the layer of skin underneath the epidermis which is called the dermis and which contains nerves and blood and lymphatic vessels. In psoriasis these blood vessels provide an increased blood supply to the abnormally multiplying keratinocytes, causing the underlying inflammation and redness characteristic of psoriasis.

Thus, psoriasis is mainly a disorder of the epidermis, which is approximately 10% of the thickness of skin overall. The remaining 90% of the skin is the dermis. The epidermis is generally about 0.12 mm thick in most areas although this value varies among individuals and different parts of the body (the hands and feet being the thickest at 1.5 mm and only 0.05 mm at the eyelids). Therefore, since the epidermis is not very thick, it is possible to effectively treat psoriasis using light that does not penetrate easily.

Thus UVA and UVB have been used to treat psoriasis with some success. However, UVC has not been used to treat psoriasis for a number of reasons as discussed below.

First, UVC penetrates much less deeply than UVA or UVB. While UVA can penetrate through the epidermis and deeply into the dermis and UVB can penetrate the epidermis and part of the dermis, most literature teaches away from UVC, indicating that UVC can only penetrate the part of the epidermis and does not reach the dermis at all (source: WHO InterSun project). However, our research with nails confirms that the penetration of UVC appears to be understated and that although most UVC cannot penetrate the full depth of the epidermis and into the epidermis, small amounts can penetrate and those amounts are sufficient to treat psoriasis and other disorders and infections.

Second, although UVC cannot penetrate very deeply, there are ways to enhance penetration such as by pulsing the light or adding a topical treatment to enhance penetration. In addition, multispectrum light can also be used to enhance penetration and to add synergistic light bands.

Third, most people skilled in the art of phototherapy with UVA and TVB do not understand that UVC is very well tolerated in dose far in excess of the minimum erythemal dose (MED). Even doses in the range of 100 MEDs will only turn the skin red—it will not be accompanied by the pain of a sunburn that even 5 MED doses of UVB can cause. The reason that UVC is so well tolerated may be because it does not penetrate well and thus mostly affect the dead cells at the top of the skin. However, that is actually an advantage when trying to treat psoriasis since this is one of the primary problem areas.

Fourth, most practitioners of phototherapy do not realize just how small a dose of UVC can be is effective. Doses in the low $mj/cm^2$ range can inactivate organisms and cells. Thus, it is not necessary to apply high, lethal doses of UVC to cells or organisms to successfully treat them.

Fifth, some practitioners are concerned that UVC may be carcinogenic. Although there is evidence of this, it should be noted that it is generally chronic exposure that is the most dangerous. However, this chronic exposure is not contemplated for treatment. Additionally it should be noted that UVA and UVB are both considered as carcinogenic as UVC, and they are regularly used in phototherapy since it is perceived that the benefits of treatment outweigh the potential risks.

Sixth, the literature teaches away from the use of UVC to treat psoriasis. For example, research was published as "Action Spectrum for the Treatment of Psoriasis" by Dr. Parrish in 1981 in the Journal of Investigative Dermatology. The research concluded that UVC was ineffective in treating psoriasis. However, several items should be noted. The first is that the maximum dosage of UVC applied was $1 J/cm^2$ which is about 50 MED. However, it is possible to apply significantly more UVC without serious side effects. Additionally, it should be noted that the sample was small—only four individuals. There is also a possibility that the filter used on the low pressure mercury lamp (the source of UVC for the test) may have decreased the effectiveness of the UVC being applied. Finally, it should be noted that only one bandwidth of UVC was used (254 nm) while the UVC range extends from 240 to 280 nm. It is probable that another wavelength within the UVC range would have elicited a much better response.

Thus, although researchers and practitioners have not used UVC for treatment of psoriasis and other disorders, there are a number of reasons that make it attractive. These reasons include the following:

a. UVC light generally only affects the epidermis and should cause little damage to the dermis. Even if the penetration of UVC is enhanced (for example by using UVC-rich pulsed polychromatic light) it will still not penetrate as deeply as many other wavelengths thereby limiting damage to deeper tissues.

b. Psoriasis is primarily a disorder of the epidermis. Thus UVC can effectively penetrate the area necessary to treat psoriasis, and since it does not penetrate more deeply, it does not elicit the painful burning reaction that UVB does. The use of screening to block application of light to only the affected ("scaling") also reduces undesired side effects, while "killing" the targeted cells.

c. UVC light is far more potent than other wavelengths of light with respect to its ability to inactivate and kill cells and organisms. Thus the dosage of UVC can be much less than would otherwise be required.

d. The application of UVC can be enhanced by pulsing of the light to permit it to penetrate more deeply and to permit smaller doses to be applied. If wideband polychromatic light is used to generate the UVC, undesirable wavelengths such as UVB can be filtered out or minimized to optimize treatment. However, if the only area being exposed has thick plaque it may be acceptable to not filter out the UVB light.

e. Application of germicidal light that includes UVC and that penetrates more deeply can also inactivate the basal cells that create an overabundance of keratinocytes thus relieving a major problem. It may also affect the T Cells that may be mediating the problem.

f. There are data that indicate that psoriasis vulgaris is mediated by activated T-lymphocytes infiltrating the epidermis and the dermo-epidermal interface. UVC can be used to treat psoriasis by infiltrating T-cells and inactivating them, where the mechanism of cell death is most probably apoptosis or damage to genetic material, which prevents the cells from reproducing.

The above reasons are illustrative and not comprehensive. They serve to show that treatment of psoriasis using germicidal light can be very attractive and effective.

5.2.3 Example 3

Using Germicidal Light to Treat Psoriasis

A recent external study of patients affected by plaque psoriasis indicated that the thickness of the epidermis averaged approximately 550 um compared to 212 um for those unaffected by psoriasis. It is not necessary to penetrate the full depth of the plaque (with screening as necessary to protect surrounding tissue) to successfully treat psoriasis, however, treatment that does penetrate more deeply is more likely to be more effective and to also require less follow up treatment.

Testing of UVC ability to penetrate nails by the applicant indicates that UVC can penetrate to a depth of 550 um, however, it should be noted that only a very small amount of unconditioned UVC will penetrate to that depth. However, broadband pulsed light can be used to successfully penetrate this depth with a much higher dose of UVC than could be delivered by a narrowband, continuous emitting low pressure mercury lamp. Therefore, this type of light would be the preferred mode of treatment.

Although there are certain cells and organisms that are significantly more difficult to inactivate due to their spore forming ability, etc., most cells and organisms are inactivated with a UVC-rich polychromatic light dose in the range of 10-40 mj/cm$^2$ total UVC dose. Since it is probable that only about 0.5% of the light will penetrate to the necessary depth it would be necessary to apply 200 times the dose that will inactivate organisms on the surface, or a dose of 2000 to 8000 mj/cm$^2$ of UVC. Approximately 10% of a highly pulsed xenon lamp is UVC, therefore, total energy dose applied would be 20 to 80 J/cm$^2$ total light. Data indicate that this dose can be tolerated by skin without discomfort. However, a similar amount of UVB will also be delivered and if this amount of light irradiates normal skin it will cause painful burns. Therefore, it would be desirable to filter out all UVB from the light to be applied. Alternately, a narrowband UVC light can be used and there will be no need to filter out the UVB. Preferably the narrowband UVC light will be highly pulsed such as that generated by a laser.

5.2.4 Additional Notes on Use of UVC to treat psoriasis

UVC can be used with PUVA to treat psoriasis. This would permit the synergistic use of these treatments which would lower the dose of each treatment individually.

UVC can be used with UVB and/or UVA to treat psoriasis. Again this would permit the combination of therapies so that doses of each individual therapy could be reduced and synergistic results obtained.

Alternating and/or combining treatment using UVC along with at least one other treatment selected from a group including wideband UVB, narrowband UVB, UVA, PUVA, topical treatments, and oral medications are other methods to treat psonasis.

5.3 Other Types of Treatment

Additionally, germicidal light can be provided to a specific location using a light guide which can also act as a scope to view the area. The light guide could be inserted remotely in a mass of tissue such as a tumor and then used to irradiate the mass with germicidal light. This will permit the inactivation and destruction of cells that are creating undesirable conditions.

Germicidal light could be introduced to the nasal cavity of a person and used to inactivate mast cells or other cells that trigger an allergic reaction. This form of treatment could be used to prevent severe allergies in a person who has an overactive immune system Germicidal light could also be introduced using a light guide to the throat to treat yeast infections, which often occur when food and breathing tubes are inserted. Specially designed breathing and food tubes could transmit the light (and are claimed as part of this invention) or the light could be introduced using a separate instrument.

Germicidal light could be used to treat warts. Although they are more difficult to treat due to their thickness, germicidal light can be applied in high doses and/or light that is more penetrating could be used.

Ringworm and other skin infections could be treated using germicidal light with the dosage being adjusted to penetrate the infection sufficiently. Techniques to lessen the thickness of the area to be treated can be used to enhance treatment such as scrubbing of the surface, abrading the area, etc. Additionally, topically applied treatments such as antibiotics could be used in conjunction with light treatment to enhance the treatment's efficacy.

Organisms that have become resistant to almost all antibiotics are an ideal candidate to be treated using this invention. Light dosage must be adjusted to ensure correct penetration and other techniques mentioned in this application to enhance efficacy can also be used.

All forms of cancer can be treated using this invention, however, the most effective treatment will occur when the mass to be treated is well defined and not too large. If the mass is large, multiple treatments or multiple points of treatment may be required. For treatment of a lump such as that in breast cancer, the device can be inserted in the middle of the mass and large amount of germicidal light be used. It should be noted that it should not be necessary to screen out UVB during this type of treatment since it should not create painful blistering. On the contrary UVB along with other synergistic wavelengths should improve treatment tremendously. Additionally, longer wavelengths of light can cause significant heating of the mass, which would be detrimental to its viability. By monitoring the temperature immediately outside the mass (by thermal imaging or probe) it should be possible to add large amounts of heat to damage the mass without sustaining permanent damage to the mass.

Germicidal light can be used to treat ulcers, warts, acne, cold sores, and other infections, diseases, and disorders that are caused by undesirable organisms or cells. It can also be used to ameliorate symptoms that include the presence of undesirable cells or organisms.

Wounds have been treated with monochromatic UVC (Johnson U.S. Pat. No. 6,283,986), however, this treatment consisted only of surface treatment since the amount of UVC used was very low and was modified to penetrate more deeply. This application claims the use of modified germicidal light (whether pulsed, wideband, and/or otherwise modified) to treat all kinds of wounds including bed sores, lacerations, ulcers, and epidermal trauma. Use of enhanced germicidal light would permit greatly enhanced treatment of wounds since it would permit inactivation and/or killing of organisms that are not on the surface, i.e. organisms that are subcutaneous or are otherwise shield from direct light.

Similar methods can be used to inactivate and kill organisms that cause disorders, diseases, and infections.

5.4 Dosages to be Applied During Treatment

A wide variety of dosages may be applied to prevent or treat skin and nail infections and disorders and to inactivate organisms and tissue that are undesirable.

For the treatment of nail infections, using the application of monochromatic UVC light has been shown to be efficacious in doses as small as 37 mj/cm$^2$ per treatment, see for example Cumbie U.S. Pat. No. 6,960,201, and as high as 22 J/cm$^2$ (as noted in this application). Additionally, these doses are well tolerated by the subject nails receiving the treatment. Allowing for smaller doses to be used for prevention of nail infections and for somewhat higher doses for severely infected nails, the applied dosage of UVC may be between approximately 10 mj/cm$^2$ and 50 J/cm$^2$ per treatment. The number of treatments may vary from 1 to 10 or more depending on the level of infection.

For treatment of nail infections using the application of modified UVC light (modified germicidal light using wide spectrum light, pulsing, etc.) the dose could be from 1% to 100% of the UVC that would be required using monochromatic UVC listed above. Thus applied dosages of UVC using modified germicidal light would be between 0.1 mj/cm$^2$ and 10 j/cm$^2$ of UVC light (not including other bands of light applied). Specifically, the amount of UVC provided by a xenon pulsed lamp has been shown to be efficacious when applied in the range of approximately 1900 mj/cm$^2$ per treatment for mild to moderate nail infections. Thus a range of approximately 500 mj/cm$^2$ to 8,000 mj/cm$^2$ of UVC delivered via a pulsed xenon light could be especially efficacious to treat many types of nail infections. The number of treatments may vary from 1 to 10 or more depending on the level of infection.

Treatment of skin and other tissue would fall in the same ranges listed above, however, for purely surface infections such as athlete's foot, this dosage could be even lower since it would not need to penetrate as deeply.

The above dosages are based on data of efficacious treatment of infections. One skilled in the art of assessing infections and disorders can apply these guidelines to deliver the correct dosage necessary to effectively prevent and treat skin and nail disorders and infections and inactivate cells or tissue that are undesirable.

6 FURTHER PREFERRED EMBODIMENTS

A further preferred embodiment of the invention would be to use germicidal light that has been enhanced to better penetrate and inactivate and kill undesirable cells. This light can be enhanced by high strength, short pulses of light that are generated by a wide spectrum light device like a xenon flash lamp. In one preferred embodiment the light would be polychromatic light that is rich in UV (especially UVC) and would be high strength (up to several Joules) and highly pulsed (multiple pulses per second such as the 120 pulses per second of some xenon flash lamps). In another preferred embodiment a reduced number of pulses would be used but each pulse would have a substantially higher peak dosage. This would increase the magnitude of energy available to exceed the energy of activation for processes that would damage or destroy the cell or organism while not increasing the average total dose delivered.

In another preferred embodiment the light would be monochromatic as generated by a laser. The laser would be tuned to provide the most germicidal light while minimizing discomfort and would also deliver short, high pulses of light.

Another preferred embodiment of the invention would be to use monochromatic germicidal light such as a low pressure mercury or an amalgam lamp that can provide substantial light to the area to be treated. Although this light would not penetrate as deeply as conditioned germicidal light it can be used for disorders that are not as deep as other disorders such as psoriasis, ringworm, or types of skin cancer that do not penetrate as deeply.

Another preferred embodiment of the invention would use filters or other means to remove unwanted bandwidths of light. This would be especially of use for treatments of disorders such as psoriasis where the use of UVB for treatment can cause painful burns.

Another preferred embodiment of the invention would be to use it for the treatment of animals.

Another preferred embodiment of the invention would be to use it for the treatment of organs to be used for transplant. Flash irradiation of the organ could decrease the potential for organ rejection as well as lowering the chance of infection.

6.1 Illustrative Germicidal Light Generators

A number of lights can be used to generate germicidal light. The list contained herein is intended to be illustrative and not exhaustive. One skilled in the art could use similar devices to generate light and such devices are claimed in this application.

Means to generate germicidal light include the following:
a. Polychromatic light sources, that generate either pulsed and continuous or both.
b. Light Emitting Diodes which are available in a number of spectrums including ones recently developed that emit in the UVC range.
c. Pulsing and Continuous Excimer Lamps including xenon-iodine (XeI or also designated as XeJ) excimer lamps emits most of its light at 253 nm, chlorine (Cl—Cl) excimer lamps emit at 258 nm, xenon-bromine (XeBr) emit at 283 nm (while this is just outside the UVC range it still have the potential to be very germicidal), xenon lamps, etc.
d. Pulsed lamps that can emit extremely strong pulses. There is evidence that it is more efficacious to have several very strong pulses instead of a number of smaller pulses. Time between the pulses can also be a significant factor and should thus be optimized.
e. Other light sources such as lasers, mercury vapor lamps, lamps that contain mercury with other elements, etc.

7 SUMMARY, RAMIFICATIONS, SCOPE

Germicidal light can be used to inactivate and kill undesirable cells permitting it to be used to treat a wide range of disorders including cancer, tumors, autoimmune disorders such as psoriasis, etc. This type of light has not been considered in the past for this type of treatment because the primary form of germicidal light which is UVC cannot easily penetrate objects and can be carcinogenic. However, UVC and other forms of germicidal light to penetrate can be enhance to improve its efficacy. Also, the possibility of germicidal light causing cancer can be minimized by preventing chronic exposure.

All references and patents identified or discussed herein are expressly incorporated by reference. To the extent that such references and patents conflict with this application, the instant specification controls.

We claim:

1. A method of treating a skin or nail infection caused by microbes, comprising: determining a dose of wide spectrum pulsed light necessary to inactivate or kill the microbes within the skin or nail;
    selecting a source of artificial light capable of providing the dose of light; and
    providing at least the dose of pulsed light sufficient to kill or inactivate some of the microbes within the skin or nail or render some of the microbes within the skin or nail substantially incapable of reproducing,
    wherein at least 1.8 J/cm2 of the light is in the range of 240 to 280 nm.

2. A method of treating a skin or nail infection caused by microbes, comprising:determining a dose of wide spectrum pulsed light necessary to inactivate or kill the microbes within the skin or nail;
    selecting a source of artificial light capable of providing the dose of light; and
    providing at least the dose of pulsed light sufficient to kill or inactivate some of the microbes within the skin or nail or render some of the microbes within the skin or nail substantially incapable of reproducing,
    wherein the dose comprises at least 4 mw/cm$^2$ of UVC light in the range of 240 to 280 nm for at least eight minutes.

3. A method of treating a skin or nail infection caused by microbes within the skin or nail, comprising:
    determining a dose of wide spectrum pulsed light necessary to inactivate or kill the microbes:
    selecting a source of artificial light capable of providing the dose of light; and providing at least the dose of pulsed light sufficient to kill or inactivate some of the microbes or render some of the microbes substantially incapable of reproducing, and wherein the total dose of light provided to the skin or nail includes at least 1.9 J/cm$^2$ of UVC light and at least one dose of light chosen from at least one of about 0.8 J/cm$^2$ of far UV from 180 nm to 240 nm; 1.9 J/cm$^2$ of UVC from 240 nm to 280 nm; 3.8 J/cm$^2$ UVB from 280 nm to 320 nm; 15 J/cm$^2$ of UVA from 320 nm to 400 nm; 113 J/cm$^2$ of visible light from 400 nm to 750 nm; 1 J/cm$^2$ of infrared from 750 nm to 880 nm; and 68 J/cm$^2$ of infrared above 880 nm.

4. A method of treating sub surface infections of a patient caused by at least one microbe, comprising:

determining the location of the infection within the skin or nail;

assessing the transmissivity of tissue at the location of the infection to UV light;

shielding tissue surrounding the location of the infection with a shield impervious to UVC light; and applying a dose of UVC light through the tissue at the location of the infection using a light source that has UVC, wherein the applied dose of UVC light renders the at least one microbe within the skin or nail substantially incapable of reproducing or kills the at least one microbe within the skin or nail.

5. A method of treating infections of a patient caused by at least one microbe within the skin or nail, comprising:

determining the location of the infection;

assessing the transmissivity of tissue at the location of the infection to UVC light;

shielding tissue surrounding the location of the infection with a shield impervious to UVC light;

calculating from the transmissivity an amount of UVC light necessary to apply a dose of electromagnetic radiation below 280 nm capable of killing the at least one microbe or rending the at least one microbe substantially incapable of reproducing; and applying the calculated amount of UVC light through the tissue at the location of the infection using a light source, wherein the applied dose of electromagnetic radiation renders the at least one microbe within the skin or nail substantially incapable of reproducing or kills the at least one microbe within the skin or nail.

* * * * *